United States Patent
Gumrukcu

(10) Patent No.: US 12,390,491 B2
(45) Date of Patent: Aug. 19, 2025

(54) COMPOSITIONS AND METHODS FOR PROVIDING CHEMOPROTECTIVE EFFECTS

(71) Applicant: GTECH BIO LLC, Los Angeles, CA (US)

(72) Inventor: Serhat Gumrukcu, Los Angeles, CA (US)

(73) Assignee: GTECH BIO LLC, Los Angeles, CA (US)

( * ) Notice: Subject to any disclaimer, the term of this patent is extended or adjusted under 35 U.S.C. 154(b) by 445 days.

(21) Appl. No.: 17/164,197

(22) Filed: Feb. 1, 2021

(65) Prior Publication Data

US 2022/0241326 A1 Aug. 4, 2022

Related U.S. Application Data

(60) Provisional application No. 62/968,906, filed on Jan. 31, 2020.

(51) Int. Cl.
| | | |
|---|---|---|
| A61K 35/17 | (2025.01) | |
| A61K 31/015 | (2006.01) | |
| A61K 31/255 | (2006.01) | |
| A61K 38/53 | (2006.01) | |
| A61K 45/06 | (2006.01) | |
| A61P 39/00 | (2006.01) | |
| C12N 9/00 | (2006.01) | |
| C12N 15/113 | (2010.01) | |

(52) U.S. Cl.
CPC ............ *A61K 35/17* (2013.01); *A61K 31/015* (2013.01); *A61K 31/255* (2013.01); *A61K 38/53* (2013.01); *A61K 45/06* (2013.01); *A61P 39/00* (2018.01); *C12N 9/93* (2013.01); *C12N 15/1138* (2013.01); *C12Y 603/02002* (2013.01); *C12N 2310/14* (2013.01); *C12N 2310/531* (2013.01)

(58) Field of Classification Search
CPC .... A61K 35/17; A61K 31/015; A61K 31/255; A61K 38/53; A61K 45/06; A61K 35/545; A61P 39/00; C12N 9/93; C12N 15/1138; C12N 2310/14; C12N 2310/531; C12Y 603/02002

See application file for complete search history.

(56) References Cited

U.S. PATENT DOCUMENTS

| | | |
|---|---|---|
| 6,268,138 B1 | 7/2001 | Dalla-Favera et al. |
| 2019/0269734 A1* | 9/2019 | Gumrukcu ........... A61K 31/675 |
| 2020/0016250 A1 | 1/2020 | Gumrukcu |

FOREIGN PATENT DOCUMENTS

| | | |
|---|---|---|
| WO | 9320195 A1 | 10/1993 |
| WO | 2015009884 A1 | 1/2015 |

OTHER PUBLICATIONS

Bansal, A and Simon, MC "Glutathione metabolism in cancer progression and treatment resistance", 2018, J. Cell. Biol., 217(7), 2291-2298. (Year: 2018).*
McCune, JS et. al. "Plasma Concentration Monitoring of Busulfan: Does It Improve Clinical Outcome?", 2000, Clin. Pharmakinet., 39(2), 155-165. (Year: 2000).*
Feins, S et. al. "An introduction to chimeric antigen receptor (CAR) T-cell immunotherapy for human cancer", 2018, Am. J. Hematol., 94, S3-S9. (Year: 2018).*
Morris, D et. al. "Glutathione synthesis is compromised in erythrocytes from individuals with HIV", 2014, Frontiers in Pharmacology, 5(73), 1-6. (Year: 2014).*
Wu, G et. al. "Glutathione Metabolism and Its Implications for Health", 2004, Journal of Nutrition, 134(3), 489-492. (Year: 2004).*
Van Wassenhove et al., "Aldehyde dehydrogenase 2 in aplastic anemia, Fanconi anemia and hematopoietic stem cells", Molecular Genetics and Metabolism, Sep. 1, 2016, vol. 119, No. 1-2, pp. 28-36.
McKinley et al., "Oral Cyclophosphamide for Lupus Glomerulonephritis: An Underused Therapeutic Option", Clin J Am Soc Nephrol. 2009, 4:1754-1760.
Jianping Zhang et al., "Handbook of Neurological Drugs", Scientific and Technical Documents Publishing House, 2000, pp. 445-446. (No English counterpart is available).
Chinese First Office Action in CN Application No. 202180020687.3, mailed Apr. 10, 2024, an English Translation attached herewith (57 pages).
Harkey M A et al: "Overexpression of Glutathione-Stransferase, MGSTII, Confers Resistance to Busulfan and Melphalan", Cancer Investigation, Taylor & Francis Inc, US, vol. 23, No. 1, Jan. 1, 2005 (Jan. 1, 2005), pp. 19-25, XP009053374, ISSN: 0735-7907.
Hiyama Noriko et al: "Glutamate-cysteine ligase catalytic subunit is associated with cisplatin resistance in lung adenocarcinoma", Japanese Journal of Clinical Oncology, vol. 48, No. 4, Apr. 1, 2018 (Apr. 1, 2018), pp. 303-307, XP093101749, DOI: 10.1093/jco/hyy013 Retrieved from the Internet: URL:https://www.ncbi.nlm.nih.gov/pmc/articles/PMC5892860/pdf/hyy013.pdf.
Gumrukcu Serhat et al: "Glutamate-Cysteine Ligase Modifier Subunit Overexpression Confers Resistance Against Busulfan", , May 1, 2022 (May 1, 2022), XP093101680, Retrieved from the Internet: URL:https://seraphinstitute.org/wp-content/uploads/2022/03/Publication10.pdf [retrieved on Nov. 15, 2023].
Botta Dianne et al: "Modulating GSH Synthesis Using Glutamate Cysteine Ligase Transgenic and Gene-Targeted Mice", Drug Metabolism Reviews, vol. 40, No. 3, Jan. 9, 2008 (Jan. 9, 2008), pp. 465-477, XP093101728, United States ISSN: 0360-2532, DOI: 10.1080/03602530802186587 Retrieved from the Internet: URL:http://dx.doi.org/10.1080/03602530802186587.

(Continued)

*Primary Examiner* — Nelson B Moseley, II
*Assistant Examiner* — Alyssa Rae Stonebraker
(74) *Attorney, Agent, or Firm* — LEASON ELLIS LLP

(57) ABSTRACT

The disclosure relates to compositions and methods for providing chemoprotective effects to target cells.

11 Claims, 7 Drawing Sheets

Specification includes a Sequence Listing.

(56) References Cited

OTHER PUBLICATIONS

Extended European Search Report in EP Application No. 21747296.8-1112/4096649, mailed Mar. 15, 2024 (18 pages).
European Patent Office Action dated Dec. 6, 2024 cited in corresponding EP Application No. 21747296.8, 8 pages.
Cortes-Wanstreet, M. et al. "Overexpression of glutamate-cystein ligase protects human COV434 granulosa tumour cells against oxidative and γ-radiation-induced cell detath", published May 1, 2009, 15 pages.
Japanese Office Action dated Dec. 24, 2024 cited in corresponding Japanese Application No. 2022-546650, 10 pages.

* cited by examiner

➤ Vector map of the lentivirus co-expressing GCLM and GFP.

➤ In vitro chemo-protection experiment model is outlined in above figure.
➤ Six independent experiments were done and representative data are shown

SEQUENCE LISTING

```
<160> NUMBER OF SEQ ID NOS: 2

<210> SEQ ID NO 1
<211> LENGTH: 274
<212> TYPE: PRT
<213> ORGANISM: Artificial Sequence
<220> FEATURE:
<223> OTHER INFORMATION: synthetic sequence

<400> SEQUENCE: 1

Met Gly Thr Asp Ser Arg Ala Ala Lys Ala Leu Leu Ala Arg Ala Arg
1               5                   10                  15

Thr Leu His Leu Gln Thr Gly Asn Leu Leu Asn Trp Gly Arg Leu Arg
            20                  25                  30

Lys Lys Cys Pro Ser Thr His Ser Glu Glu Leu His Asp Cys Ile Gln
        35                  40                  45

Lys Thr Leu Asn Glu Trp Ser Ser Gln Ile Asn Pro Asp Leu Val Arg
    50                  55                  60

Glu Phe Pro Asp Val Leu Glu Cys Thr Val Ser His Ala Val Glu Lys
65                  70                  75                  80

Ile Asn Pro Asp Glu Arg Glu Glu Met Lys Val Ser Ala Lys Leu Phe
                85                  90                  95

Ile Val Glu Ser Asn Ser Ser Ser Thr Arg Ser Ala Val Asp Met
            100                 105                 110

Ala Cys Ser Val Leu Gly Val Ala Gln Leu Asp Ser Val Ile Ile Ala
        115                 120                 125

Ser Pro Pro Ile Glu Asp Gly Val Asn Leu Ser Leu Glu His Leu Gln
    130                 135                 140

Pro Tyr Trp Glu Glu Leu Glu Asn Leu Val Gln Ser Lys Lys Ile Val
145                 150                 155                 160
```

```
Ala Ile Gly Thr Ser Asp Leu Asp Lys Thr Gln Leu Glu Gln Leu Tyr
            165                 170                 175

Gln Trp Ala Gln Val Lys Pro Asn Ser Asn Gln Val Asn Leu Ala Ser
        180                 185                 190

Cys Cys Val Met Pro Pro Asp Leu Thr Ala Phe Ala Lys Gln Phe Asp
            195                 200                 205

Ile Gln Leu Leu Thr His Asn Asp Pro Lys Glu Leu Leu Ser Glu Ala
        210                 215                 220

Ser Phe Gln Glu Ala Leu Gln Glu Ser Ile Pro Asp Ile Gln Ala His
225                 230                 235                 240

Glu Trp Val Pro Leu Trp Leu Leu Arg Tyr Ser Val Ile Val Lys Ser
            245                 250                 255

Arg Gly Ile Ile Lys Ser Lys Gly Tyr Ile Leu Gln Ala Lys Arg Arg
            260                 265                 270

Gly Ser
```

<210> SEQ ID NO 2
<211> LENGTH: 5066
<212> TYPE: DNA
<213> ORGANISM: Artificial Sequence
<220> FEATURE:
<223> OTHER INFORMATION: synthetic sequence

<400> SEQUENCE: 2

```
acccgtcgcc acgcccgccg caggccaagg gccagtcact tgcgggccgg cgtcccgcag      60
cccattcgcg ccccgcccct gccccgccgc gggatgagta acggttacga agcactttct     120
cggctacgat ttctgcttag tcattgtctt ccaggaaaca gctccctcag tttggaatca     180
gctctcccgc tgcggccgca gtagccgag ccggagccgc agccaccggt gccttccttt      240
cccgccgccg cccagccgcc gtccggcctc cctcgggccc gagcgcagac caggctccag     300
ccgcgcggcg ccggcagcct cgcgctccct ctcgggtctc tctcgggcct cgggcaccgc     360
gtcctgtggg gcggccgcct gcctgcccgc cgcccgcag ccccttcgct gcgcggcccc      420
tgggcggccg ctgccatggg caccgacagc cgcgcggcca aggcgctcct ggcgcgggcc     480
cgcaccctgc acctgcagac ggggaacctg ctgaactggg gccgcctgcg gaagaagtgc     540
ccgtccacgc acagcgagga gcttcatgat tgtatccaaa aaaccttgaa tgaatggagt     600
tcccaaatca acccagattt ggtcaggag tttccagatg tcttggaatg cactgtatct      660
catgcagtag aaaagataaa tcctgatgaa agagaagaaa tgaaagtttc tgcaaaactg     720
ttcattgtag aatcaaactc ttcatcatca actagaagtg cagttgacat ggcctgttca     780
gtccttggag ttgcacagct ggattctgtg atcattgctt cacctcctat gaagatgga     840
gttaatcttt ccttggagca tttacagcct tactgggagg aattagaaaa cttagttcag     900
agcaaaaaga ttgttgccat aggtacctct gatctagaca aaacacagtt ggaacagctg     960
tatcagtggg cacaggtaaa accaaatagt aaccaagtta atcttgcctc tgctgtgtg     1020
atgccaccag atttgactgc atttgctaaa caatttgaca tacagctgtt gactcacaat    1080
gatccaaaag aactgctttc tgaagcaagt ttccaagaag ctcttcagga aagcattcct    1140
gacattcaag cgcacgagtg ggtgccgctg tggctactgc ggtattcggt cattgtgaaa    1200
agtagaggaa ttatcaaatc aaaaggctac attttacaag ctaaagaag gggttcttaa     1260
ctgacttagg agcataactt acctgtaatt tccttcaata tgagagaaaa ttgagatgtg    1320
taaaaatcta gttactgcct gtaaatggtg tcattgaggc agatattctt tcgtcatatt    1380
```

-continued

```
tgacagtatg ttgtctgtca agtttaaat acttatcttg cctccatatc aatccattct  1440
catgaacctc tgtattgctt tccttaaact attgttttct aattgaaatt gtctataaag  1500
aaaatacttg caatatattt ttcctttatt tttatgacta atataaatca agaaaatttg  1560
ttgttagata tattttggcc taggtatcag ggtaatgtat atacatattt tttatttcca  1620
aaaaaaattc attaattgct tcttaactct tattataacc aagcaattta attacaattg  1680
ttaaaactga atactggaa gaagatattt ttcctgtcat tgatgagata tatcagagta  1740
actggagtag ctgggattta ctagtagtgt aaataaaatt cactcttcaa tacatgaatg  1800
gaaacttaaa ttttttttta tgtgtccttg cttatagttt agctgtaata atttaacctt  1860
gtattcttgt gccatattct gtctttttat tacttataaa gacaaaccaa agtaaatctg  1920
aaaggagact agaagctttg aaattattgt ttggggtttt tataaaagca actactgtca  1980
cctccatcca gattctttta aattattgat ccatccatag tatatattgc tactcattca  2040
agaatcctca ataagtattg agtatttacc atatgttggg atactgtggg ctctggagag  2100
aggagggggc aatagagcta ggaattaaga atcagttgag taaaatgtgt aatatttatt  2160
ccccattaat aactgactag gaaggactaa aagccagaaa ggggatgaaa aaaaaatcct  2220
taattcaggg ccgacattat ctacttaaac aactttgaga tatggtctta attattttaa  2280
agcagaataa tataattgaa agtttatagc taaaagagac tatataggtc atttagtata  2340
attcttcatt agtttacgaa ccacaaaatt gcaaataaat aagctatgaa ctttgatgta  2400
cactataaat ctccttaatt ctataaattt gtgtctgtaa cctgaatagt ttgaaaactt  2460
ctttaaaaat ctcttgtatt tcatccgggc gcagtggctc acacctgtaa tcccagcact  2520
ttgggaggcc gaggtgggca gatcacgagg tcaggagttt gagaccagcc tgaccaacat  2580
ggtaaaaccc catctctact aaaatacaaa aattggctgg gcgtggtggc actcgcctgt  2640
aatctcagct acttgggagg ctgaggcagg agaatcgctt gaacccggga ggcggaggtt  2700
acagtgagcc gagatcacat cactgcactc cagcctgggc gacagagcga gactccatct  2760
caaaaaaaa aaaaaactct tgtatctcaa tatttttaaa ccacaggcct aaataaaact  2820
aatttttgctc aagtttttctc aacctaggga aaaagaacta tggttccata ttcaaaataa  2880
atattataga ccccttttcct aagtaggatt ttgtggttta ctgattgggt aatttgatca  2940
ttaaaattat gtgaaatctg cccgggcaca cctcatgcct gtaatcccag cactctggga  3000
ggccaaggca gatgatcacc tgaggtcagg agttctagac cagcctggct aacatggtga  3060
aaccctgtat ctgctaaaaa tacaaaaatt agccaggcgt ggtggcgggc tcctgtaatc  3120
ccagctactt tggaggcgag gcacgagaat cgcttgaacc tgggaggcgg agtttgcagt  3180
gagccgagat cacgccattg cactccagcc tgggcgacag agcgagactg cgtctcaaaa  3240
aaaaaaaaa aagaaaaatt atgtgaaatc atgtgatttg cctgggaaaa cttgtttaga  3300
tattgagcta cttatgcctt ctagcctttta tattaattgt atgtaatgtt attaaatata  3360
tatatagttc atctttacat ttggaaatgc ccaacatttt tttcatataa gtccttaaac  3420
aagcgttcat tttattttaa atctatacag tgaactggcc aagatatttt aagagggaac  3480
tttaatatcc catttattgt tttttataacc ctggacttat aaaaatgggt tgtttgaagg  3540
gttattttga aagtgggga aaaaaaact tagttgctaa tgtatctaaa cttcagcaga  3600
gcttttttggt gatctcctac ctgcaccctc aactcttgac aaagaagcaa gactatagat  3660
tcattttctg aaggggatca tgtatggaat ttttgatga gttttacttt ttacctctct  3720
actcttgatt ttctattatt gaatactctt ttaaaacact gatttttaag gctttatata  3780
```

```
tgttttccag gctgatgttc acatcttttt ttcatgaact atcagaatat agtgaacact    3840
tttcaaatat ttaaggactt aatgtttaaa aagccataaa atagagagtg gtaatactac    3900
caaataatta cttaaaactg aaagctaagt tatcaatagt ttatataaga gatgttttct    3960
gaggagatgt gcatccagtg agaccaaggt agaaagttta tataattgtt ttttttccag    4020
taaatatgaa aaaaaagct gtagcttgtt tattacatgt ccaaaataca gtggagcctt    4080
actttaacac aatgtactgt aacttggaat ttgttctgtt atgagtctat cttgaattcc    4140
catccatgaa actgtagtca ccaaaagcaa caagtattt cacatgatgt aaaagaccat    4200
actatgatgg ccattgctag aaattgaatc acaaataata gctaataatt tttcattttt    4260
caaaaaagat catttggata gcagctatgt ataaaatgga aaataaaaaa ttattctatt    4320
ttgcatgaat agttcagact ttcccatacc acagccaagc agtaactaaa attaggatct    4380
taattttcaa tgataaaagg tctaaggttc atttaattat gctcctttaa cactgtcttt    4440
ctagattttt cacccagtat tttcaaaatt tgggaatgta aacaattgat atatttattg    4500
tatgttggct agcagttcat ccttctgcaa aatatgcatt cagagaaatg tgaagcttgt    4560
tttaatgaag acttaaacca tttgtgtcat ttgtgttttc atattcaaat acaccaaatt    4620
aaaattctga acctatattt ttcatcatta acttcctaat ataccagaac atataccttt    4680
ttcatgtaaa gttggcaatg ggatatggca gttttatttt tgaaaaatat gtaacatgac    4740
tttaatattt ttatagtttt cagaattaga aacataggaa gggaaaatgt tttaattaga    4800
taagtcaact ttttatgtgt ctgtagtggt gtactataat agcaaattat aaagcattat    4860
taaatgttta taataatttt taatattacc tacattatga atttaactaa aataaagtgt    4920
gagttgtata ttttttaatt gggttgtttc aatagctgga agcatcctga agcattatat    4980
tgatttttga actatttgaa ctcaaactga gtatgatttg aaaataaatt aataatttaa    5040
aaacatccaa aaaaaaaaaa aaaaaa                                          5066
```

COMPOSITIONS AND METHODS FOR PROVIDING CHEMOPROTECTIVE EFFECTS

CROSS-REFERENCE TO RELATED APPLICATIONS

This application claims priority to U.S. Provisional Application No. 62/968,906, filed Jan. 31, 2020, which is hereby incorporated by reference in its entirety.

FIELD

The disclosure relates to compositions and methods for providing chemoprotective effects to target cells.

BACKGROUND

A tremendous obstacle in gene-modified stem cell therapies is lack of sufficient engraftment. One proposed solution is giving these cells chemo-resistance against cytotoxic agents to select them in vivo. However, finding a single resistance gene that confers sufficient resistance against agents particularly toxic to hematopoietic stem/progenitor cells (HSPCs) has been challenging. Genes that give multidrug resistance can give promising results, but they come with safety concerns. Busulfan is mostly used for conditioning regimens in HSPC transplants due to its profound toxicity to HSPCs. Thus, improved chemoprotectant compositions and methods are badly needed.

SUMMARY

Provided herein are methods and compositions for providing or improving chemoprotection in a target cell. In some embodiments, the methods comprise providing a heterologous glutamate-cysteine ligase (GCL) modifier subunit (GCLM), GCLC (GCL catalytic subunit), GCL (as a dimer or a full enzyme), or any other polypeptide in the GSH synthesis pathway that provide the equivalent function. In some embodiments, the heterologous gene/protein is GCLM.

In some embodiments, methods for providing or improving chemoprotection in a patient in need thereof are provided. In some embodiments, the methods comprise administering to the patient a heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function. In some embodiments, the heterologous gene/protein is GCLM.

Additional embodiments provide transgene expression of glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function and allows for post-transplant in vivo selection.

Further embodiments provide that the cells are stem cells or immune cells.

In some embodiments, the stem cell are fetal stem cells, cord blood derived stem cells, hematopoietic stem cells (HSCs), pluripotent stem cells (PSCs), induced PSCs (iPSCs), embryonic stem cells (ESCs) or cells derived therefrom, such as CD34+ cells, CD90+ cells, CD45+ cells, CD17+ cells, CD45RA− cells, or any combination thereof.

In some embodiments, the immune cells are T cells.

In some embodiments, the modified cells are autologous to the patient, allogeneic to the patient, or a combination thereof.

In some embodiments, the method further comprises contacting unmodified cells with an expression vector encoding for the expression of glutamate-cysteine ligase (GCL) modifier subunit GCLM, GCLC (GCL catalytic subunit), GCL (as a dimer or a full enzyme), or other polypeptide in the GSH synthesis pathway that provide the equivalent function. In some embodiments, the expression vector encodes for GCLM.

In some embodiments, the expression vector is a viral vector or a non-viral vector.

In some embodiments, the viral vector is a lentiviral or adenoviral vector.

In some embodiments, the expression vector is a retrovirus, a transposon, an episomal expression vector, modified RNA, a plasmid, or any combination thereof.

In some embodiments, the patient is undergoing gene therapy, cell therapy, or CAR-T therapy.

In some embodiments, the chemoprotection provided is to busulfan and/or naphthalene.

BRIEF DESCRIPTION OF DRAWINGS

FIG. 4 shows that there was a 1.7 fold increase in GSH level in GCLM-transduced cells and that the GSH level remained at least 3.5-fold higher in transduced cells at different dose and time at 24-hr post busulfan exposure.

DETAILED DESCRIPTION

Figure 1:
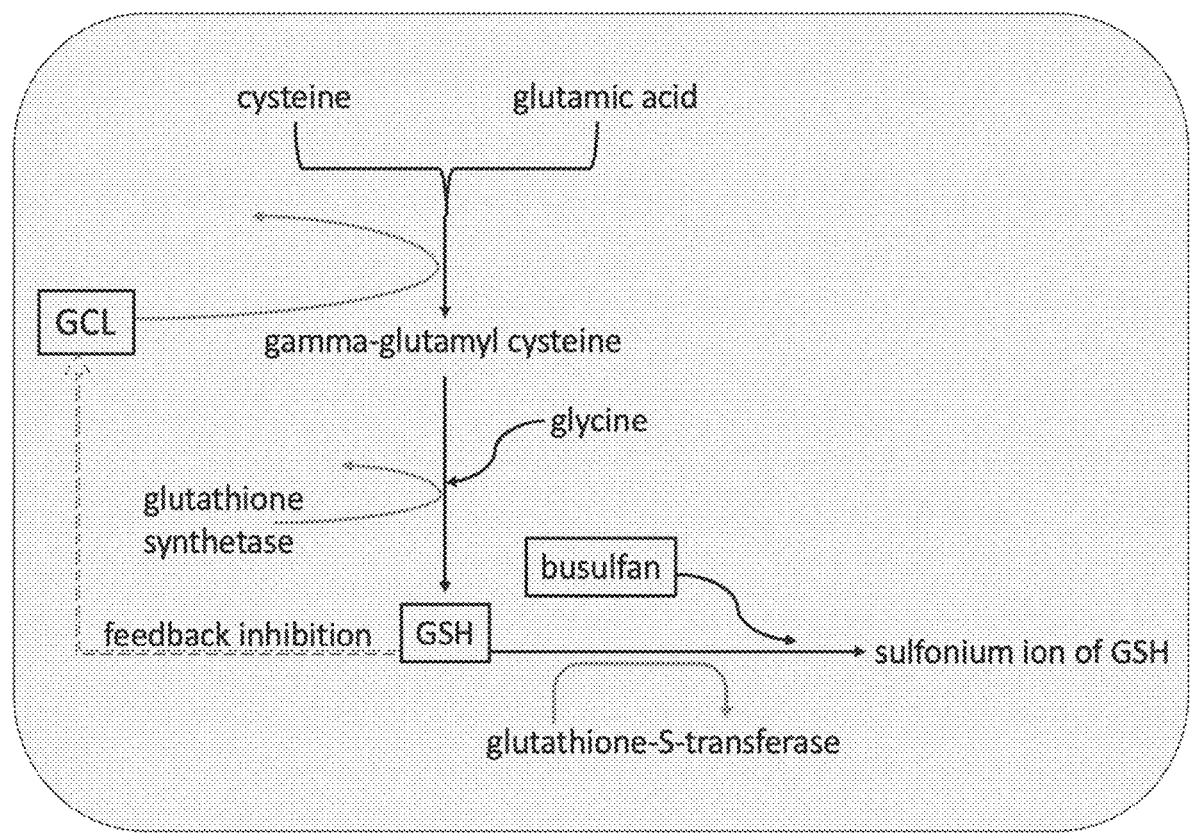
FIG. 1 illustrates the glutathione synthesis pathway and the utilization of busulfan.

It is to be understood, although not always explicitly stated that all numerical designations are preceded by the term "about." As used herein, the term "about" means that the numerical value is approximate and small variations would not significantly affect the practice of the disclosed embodiments.

It must be noted that as used herein and in the appended claims, the singular forms "a", "an", and "the" include plural referents unless the context clearly dictates otherwise. Thus, for example, reference to "a cell" includes a plurality of cells.

Definitions

As used herein the following terms have the following meanings.

The term "about" when used before a numerical designation, e.g., temperature, time, amount, concentration, and such other, including a range, indicates approximations which may vary by (+) or (−) 20%, 10%, 5% or 1%.

Also as used herein, "and/or" refers to and encompasses any and all possible combinations of one or more of the associated listed items, as well as the lack of combinations when interpreted in the alternative ("or").

The terms "administering," "administer" and the like refer to introducing an agent (e.g., a cell) into a subject. Typically, an effective amount is administered, which amount can be determined by the treating physician or the like. Any route of administration, such as topical, subcutaneous, peritoneal, intravenous, intraarterial, inhalation, vaginal, rectal, nasal, oral, buccal, introduction into the cerebrospinal fluid, or instillation into body compartments can be used. The terms and phrases "administering" and "administration of," when used in connection with a composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer an agent (e.g., a cell) and/or provides a patient with a prescription for a drug is administering the agent to the patient. "Periodic administration" or "periodically administering" refers to multiple treatments that occur on a daily, weekly, or a monthly basis. Periodic administration may also refer to administration of an agent one, two, three or more time(s) per day.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Any step or composition that uses the transitional phrase of "comprise" or "comprising" can also be said to describe the same with the transitional phase of "consisting of" or "consists."

An "effective amount" is an amount of an agent or compound (e.g., cell or population of cells) sufficient to effect beneficial or desired results. An effective amount can be in one or more administrations, applications or doses. Determination of these parameters is well within the skill of the art. These considerations, as well as effective formulations and administration procedures are well known in the art and are described in standard textbooks.

The term "heterologous" when referencing a nucleic acid molecule, protein, vector, or expression cassette refers to a nucleic acid molecule, protein, vector, or expression cassette that is expressed in a cell through the manipulation of a user and is not naturally occurring. For example, a heterologous gene refers to a gene that is expressed by a vector or other vehicle that is put in the cell or to a gene that is in the genome that has been modified through a gene editing methods, such as CRISPR, or other recombination techniques to replace the gene in a cell. One of skill in the art would understand that the term "heterologous" does not refer to a naturally occurring gene in the genome of a cell that has not been modified. "Heterologous" can also be referred to as "exogenous." Therefore, in some embodiments, a cell can express the same protein both heterologously and from its own genome (endogenous).

The term "isolated" as used herein with respect to nucleic acids, such as DNA or RNA, refers to molecules separated from other DNAs or RNAs, respectively that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. An "isolated cell," for example, an isolated bone marrow cell is a cell that is substantially free of other cellular material, tissue, medium of the environment in which it is naturally found.

The term "myeloablative" means a treatment that causes long lasting (usually irreversible) pancytopenia, kills cells in the bone marrow within 1 to 3 weeks from administration, and does not allow autologous hematologic recovery. Bacigalupo et al., *Biol Blood Marrow Transplant.* 2009, 15(12): 1628-1633. Examples of myeloablative doses of cyclophosphamide include, without limitation, 2.5 mg/kg/day CTX or greater for a period of time that results in cumulative toxicity (McKinley et al., *Clin J Am Soc Nephrol.* 2009, 4:1754-1760).

The term "non-myeloablative" means a treatment that causes no, minimal, or reversible cytopenia with little toxicity. Non-myeloablative regimens are immuno-ablation. Examples of non-myeloablative doses include, without limitation, approximately 1.3 mg/kg/day for a period of time that does not result in cumulative toxicity or 1.0 to 1.5 mg/kg/day for 2 to 4 months (McKinley et al., *Clin J Am Soc Nephrol.* 2009, 4:1754-1760). Other non-myeloablative doses are described throughout and are included within the definition of non-myeloablative doses. An agent or dose of an agent that results in "cumulative toxicity" refers to a dose that over time will lead to toxicity in the patient. For example, cyclophosphamide that is administered to a human at a dose of 2.5 mg/kg/day for a period of weeks will lead to cumulative toxicity. Other examples of a non-myeloablative doses can be found, for example, in U.S. Publication No. 2019/0269734, which is hereby incorporated by reference in its entirety.

A "subject," "individual" or "patient" is used interchangeably herein and refers to a vertebrate, for example a primate, a mammal or preferably a human. Mammals include, but are not limited to equines, canines, bovines, ovines, murines, rats, simians, and humans.

The term "sequence identity" with respect to a protein or amino acid sequence (or a DNA or RNA sequence) refers to the percentage of amino acid residues (or nucleotide residues) in a candidate sequence that are identical to the amino acid residues in the specific protein or amino acid sequence (or nucleotide residues in the specific DNA or RNA sequence), after aligning the sequences and introducing gaps, if necessary, to achieve a maximum percent sequence identity, and not considering any conservative substitutions as part of the sequence identity. Alignment can be achieved by any method known to one of skill in the art, for example, by using publicly available programs such as BLAST and EMBOSS. Those skilled in the art can determine appropriate parameters for measuring alignment, including any algorithms needed to achieve maximal alignment over the full length of the sequences being compared, but in some embodiments, the default parameters are used. The programs can be accessed for example at the National Center for Biotechnology Information.

The term "variant" as used herein, is a nucleic acid or protein that differs from a reference nucleic acid or protein, but retains essential properties (i.e., biological activity). A typical variant of a polynucleotide differs in nucleotide sequence from another, reference polynucleotide. Changes in the nucleotide sequence may or may not alter the amino acid sequence of a polypeptide encoded by the reference polynucleotide. Nucleotide changes may result in amino acid substitutions, additions, deletions, fusions, and/or truncations in the polypeptide encoded by the reference sequence.

The term "vector" is used herein to refer to a nucleic acid molecule capable of transferring or transporting another nucleic acid molecule. The transferred nucleic acid is generally linked to, for example, the vector nucleic acid molecule. A vector may include sequences that direct autonomous replication in a cell, or may include sequences sufficient to allow integration into cellular DNA. Vectors include, for example, plasmids (e.g., DNA plasmids or RNA plasmids), transposons, cosmids, bacterial or yeast artificial chromosomes and viral vectors. Useful viral vectors include, for example, adenoviruses, retroviruses, such as, but not limited to, replication defective retroviruses, and lentiviruses.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein the term, "GCLM" when referring to the protein form, refers to a protein comprising the sequence of SEQ ID NO: 1 or a variant thereof.

```
                                              (SEQ ID NO: 1)
MGTDSRAAKALLARARTLHLQTGNLLNWGRLRKKCPSTHSEELH

DCIQKTLNEWSSQINPDLVREFPDVLECTVSHAVEKINPDEREE

MKVSAKLFIVESNSSSSTRSAVDMACSVLGVAQLDSVIIASPPI

EDGVNLSLEHLQPYWEELENLVQSKKIVAIGTSDLDKTQLEQLY

QWAQVKPNSNQVNLASCCVMPPDLTAFAKQFDIQLLTHNDPKEL

LSEASFQEALQESIPDIQAHEWVPLWLLRYSVIVKSRGIIKSKG

YILQAKRRGS
```

In some embodiments, the GCLM protein is at least 90%, 91%, 92%, 93%, 94%, 95%, 96%, 97%, 98%, or 99% identical or substantially identical to SEQ ID NO: 1. The sequence of the protein is also provided for in Genbank Accession No. NM_002061.3 or NP_002052.1, each of which is hereby incorporated by reference in its entirety.

Genbank Accession No. NM_002061.3 provides for one example of a nucleic acid molecule that can encode for SEQ ID NO: 1.

As used herein the term, "GCLM" when referring to a nucleotide form, refers to a nucleic acid molecule that encodes for GCLM. In some embodiments, the nucleic acid molecule comprising the sequence of SEQ ID NO: 2 or a variant thereof, wherein such variant can be substantially identical to SEQ ID NO: 2. Because the genetic code has degeneracy, SEQ ID NO: 2 is a non-limiting example and other nucleotide sequences can be used to encode the GCLM protein or a protein that is identical or substantially identical to the protein. SEQ ID NO: 2 is as follows:

```
                                              (SEQ ID NO: 2)
ACCCGTCGCCACGCCCGCCGCAGGCCAAGGGCCAGTCACTTGCGGGCCGG

CGTCCCGCAGCCCATTCGCGCCCCGCCCCTGCCCCGCCGCGGGATGAGTA

ACGGTTACGAAGCACTTTCTCGGCTACGATTTCTGCTTAGTCATTGTCTT

CCAGGAAACAGCTCCCTCAGTTTGGAATCAGCTCTCCCGCTGCGGCCGCA

GTAGCCGGAGCCGGAGCCGCAGCCACCGGTGCCTTCCTTTCCCGCCGCCG

CCCAGCCGCCGTCCGGCCTCCCTCGGGCCCGAGCGCAGACCAGGCTCCAG

CCGCGCGGCGCCGGCAGCCTCGCGCTCCCTCTCGGGTCTCTCTCGGGCCT

CGGGCACCGCGTCCTGTGGGGCGGCCGCCTGCCTGCCCGCCCGCCCGCAG

CCCCTTCGCTGCGCGGCCCCTGGGCGGCCGCTGCCATGGGCACCGACAGC

CGCGCGGCCAAGGCGCTCCTGGCGCGGGCCCGCACCCTGCACCTGCAGAC

GGGGAACCTGCTGAACTGGGGCCGCCTGCGGAAGAAGTGCCCGTCCACGC

ACAGCGAGGAGCTTCATGATTGTATCCAAAAAACCTTGAATGAATGGAGT

TCCCAAATCAACCCAGATTTGGTCAGGGAGTTTCCAGATGTCTTGGAATG

CACTGTATCTCATGCAGTAGAAAAGATAAATCCTGATGAAAGAGAAGAAA

TGAAAGTTTCTGCAAAACTGTTCATTGTAGAATCAAACTCTTCATCATCA

ACTAGAAGTGCAGTTGACATGGCCTGTTCAGTCCTTGGAGTTGCACAGCT

GGATTCTGTGATCATTGCTTCACCTCCTATTGAAGATGGAGTTAATCTTT

CCTTGGAGCATTTACAGCCTTACTGGGAGGAATTAGAAAACTTAGTTCAG

AGCAAAAAGATTGTTGCCATAGGTACCTCTGATCTAGACAAAACACAGTT

GGAACAGCTGTATCAGTGGGCACAGGTAAAACCAAATAGTAACCAAGTTA

ATCTTGCCTCCTGCTGTGTGATGCCACCAGATTTGACTGCATTTGCTAAA

CAATTTGACATACAGCTGTTGACTCACAATGATCCAAAAGAACTGCTTTC

TGAAGCAAGTTTCCAAGAAGCTCTTCAGGAAAGCATTCCTGACATTCAAG

CGCACGAGTGGGTGCCGCTGTGGCTACTGCGGTATTCGGTCATTGTGAAA

AGTAGAGGAATTATCAAATCAAAAGGCTACATTTTACAAGCTAAAAGAAG

GGGTTCTTAACTGACTTAGGAGCATAACTTACCTGTAATTTCCTTCAATA

TGAGAGAAAATTGAGATGTGTAAAAATCTAGTTACTGCCTGTAAATGGTG

TCATTGAGGCAGATATTCTTTCGTCATATTTGACAGTATGTTGTCTGTCA

AGTTTTAAATACTTATCTTGCCTCCATATCAATCCATTCTCATGAACCTC

TGTATTGCTTTCCTTAAACTATTGTTTTCTAATTGAAATTGTCTATAAAG

AAAATACTTGCAATATATTTTTCCTTTATTTTTATGACTAATATAAATCA
```

```
AGAAAATTTGTTGTTAGATATATTTTGGCCTAGGTATCAGGGTAATGTAT
ATACATATTTTTTATTTCCAAAAAAAATTCATTAATTGCTTCTTAACTCT
TATTATAACCAAGCAATTTAATTACAATTGTTAAAACTGAAATACTGGAA
GAAGATATTTTTCCTGTCATTGATGAGATATATCAGAGTAACTGGAGTAG
CTGGGATTTACTAGTAGTGTAAATAAAATTCACTCTTCAATACATGAATG
GAAACTTAAATTTTTTTTATGTGTCCTTGCTTATAGTTTAGCTGTAATA
ATTTAACCTTGTATTCTTGTGCCATATTCTGTCTTTTTATTACTTATAAA
GACAAACCAAAGTAAATCTGAAAGGAGACTAGAAGCTTTGAAATTATTGT
TTGGGGGTTTTATAAAAGCAACTACTGTCACCTCCATCCAGATTCTTTTA
AATTATTGATCCATCCATAGTATATATTGCTACTCATTCAAGAATCCTCA
ATAAGTATTGAGTATTTACCATATGTTGGGATACTGTGGGCTCTGGAGAG
AGGAGGGGGCAATAGAGCTAGGAATTAAGAATCAGTTGAGTAAAATGTGT
AATATTTATTCCCCATTAATAACTGACTAGGAAGGACTAAAAGCCAGAAA
GGGGATGAAAAAAAAATCCTTAATTCAGGGCCGACATTATCTACTTAAAC
AACTTTGAGATATGGTCTTAATTATTTTAAAGCAGAATAATATAATTGAA
AGTTTATAGCTAAAAGAGACTATATAGGTCATTTAGTATAATTCTTCATT
AGTTTACGAACCACAAAATTGCAAATAAATAAGCTATGAACTTTGATGTA
CACTATAAATCTCCTTAATTCTATAAATTTGTGTCTGTAACCTGAATAGT
TTGAAAACTTCTTTAAAAATCTCTTGTATTTCATCCGGGCGCAGTGGCTC
ACACCTGTAATCCCAGCACTTTGGGAGGCCGAGGTGGGCAGATCACGAGG
TCAGGAGTTTGAGACCAGCCTGACCAACATGGTAAAACCCCATCTCTACT
AAAATACAAAAATTGGCTGGGCGTGGTGGCACTCGCCTGTAATCTCAGCT
ACTTGGGAGGCTGAGGCAGGAGAATCGCTTGAACCCGGGAGGCGGAGGTT
ACAGTGAGCCGAGATCACATCACTGCACTCCAGCCTGGGCGACAGAGCGA
GACTCCATCTCAAAAAAAAAAAAAAACTCTTGTATCTCAATATTTTTAAA
CCACAGGCCTAAATAAAACTAATTTTGCTCAAGTTTTCTCAACCTAGGGA
AAAAGAACTATGGTTCCATATTCAAAATAAATATTATAGACCCTTTTCCT
AAGTAGGATTTTGTGGTTTACTGATTGGGTAATTTGATCATTAAAATTAT
GTGAAATCTGCCCGGGCACACCTCATGCCTGTAATCCCAGCACTCTGGGA
GGCCAAGGCAGATGATCACCTGAGGTCAGGAGTTCTAGACCAGCCTGGCT
AACATGGTGAAACCCTGTATCTGCTAAAAATACAAAAATTAGCCAGGCGT
GGTGGCGGGCTCCTGTAATCCCAGCTACTTTGGAGGCGAGGCACGAGAAT
CGCTTGAACCTGGGAGGCGGAGTTTGCAGTGAGCCGAGATCACGCCATTG
CACTCCAGCCTGGGCGACAGAGCGAGACTGCGTCTCAAAAAAAAAAAAA
AAGAAAAATTATGTGAAATCATGTGATTTGCCTGGGAAAACTTGTTTAGA
TATTGAGCTACTTATGCCTTCTAGCCTTTATATTAATTGTATGTAATGTT
ATTAAATATATATATAGTTCATCTTTACATTTGGAAATGCCCAACATTTT
TTTCATATAAGTCCTTAAACAAGCGTTCATTTTATTTTAAATCTATACAG
TGAACTGGCCAAGATATTTTAAGAGGGAACTTTAATATCCCATTTATTGT
TTTTATAACCCTGGACTTATAAAAATGGGTTGTTTGAAGGGTTATTTTGA
AAGTGGGGAAAAAAAAACTTAGTTGCTAATGTATCTAAACTTCAGCAGA
GCTTTTTGGTGATCTCCTACCTGCACCCTCAACTCTTGACAAAGAAGCAA
GACTATAGATTCATTTTCTGAAGGGGATCATGTATGGAATTTTTTGATGA
GTTTTTACTTTTACCTCTCTACTCTTGATTTTCTATTATTGAATACTCTT
TTAAAACACTGATTTTTAAGGCTTTATATATGTTTTCCAGGCTGATGTTC
ACATCTTTTTTTCATGAACTATCAGAATATAGTGAACACTTTTCAAATAT
TAAGGACTTAATGTTTAAAAAGCCATAAAATAGAGAGTGGTAATACTACC
AAATAATTACTTAAAACTGAAAGCTAAGTTATCAATAGTTTATATAAGAG
ATGTTTTCTGAGGAGATGTGCATCCAGTGAGACCAAGGTAGAAAGTTTAT
ATAATTGTTTTTTTTCCAGTAAATATGAAAAAAAAAGCTGTAGCTTGTTT
ATTACATGTCCAAAATACAGTGGAGCCTTACTTTAACACAATGTACTGTA
ACTTGGAATTTGTTCTGTTATGAGTCTATCTTGAATTCCCATCCATGAAA
CTGTAGTCACCAAAAGCAACAAGTATTTTCACATGATGTAAAAGACCATA
CTATGATGGCCATTGCTAGAAATTGAATCACAAATAATAGCTAATAATTT
TTCATTTTTCAAAAAAGATCATTTGGATAGCAGCTATGTATAAAATGGAA
AATAAAAAATTATTCTATTTTGCATGAATAGTTCAGACTTTCCCATACCA
CAGCCAAGCAGTAACTAAAATTAGGATCTTAATTTTCAATGATAAAAGGT
CTAAGGTTCATTTAATTATGCTCCTTTAACACTGTCTTTCTAGATTTTTC
ACCCAGTATTTTCAAAATTTGGGAATGTAAACAATTGATATATTTATTGT
ATGTTGGCTAGCAGTTCATCCTTCTGCAAAATATGCATTCAGAGAAATGT
GAAGCTTGTTTTAATGAAGACTTAAACCATTTGTGTCATTTGTGTTTTCA
TATTCAAATACACCAAATTAAAATTCTGAACCTATATTTTTCATCATTAA
CTTCCTAATATACCAGAACATATACCTTTTTCATGTAAAGTTGGCAATGG
GATATGGCAGTTTTATTTTTGAAAAATATGTAACATGACTTTAATATTTT
TATAGTTTTCAGAATTAGAAACATAGGAAGGGAAAATGTTTTAATTAGAT
AAGTCAACTTTTTATGTGTCTGTAGTGGTGTACTATAATAGCAAATTATA
AAGCATTATTAAATGTTTATAATAATTTTTAATATTACCTACATTATGAA
TTTAACTAAAATAAAGTGTGAGTTGTATATTTTTTAATTGGGTTGTTTCA
ATAGCTGGAAGCATCCTGAAGCATTATATTGATTTTTGAACTATTTGAAC
TCAAACTGAGTATGATTTGAAAATAAATTAATAATTTAAAAACATCCAAA
AAAAAAAAAAAAAA.
```

In some embodiments, the nucleotide sequence comprises the coding region of SEQ ID NO: 2, which is nucleotides 436 to 1260 of SEQ ID NO: 2. In some embodiments, the nucleic acid molecule only comprises the coding region of SEQ ID NO: 2 or a sequence that encodes the GCLM protein, or a variant thereof. The variant, as described herein, can have substitutions or mutations. In some embodiments, the substitutions are conservative substitutions. In some embodiments, the GCLM protein variant is substantially identical to SEQ ID NO: 1.

Sequence identity, percentage identity, and related terms, as those terms are used herein, refer to the relatedness of two sequences, e.g., two nucleic acid sequences or two amino acid or polypeptide sequences. In the context of an amino acid sequence, the term "substantially identical" is used herein to refer to a first amino acid that contains a sufficient or minimum number of amino acid residues that are i)

identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein, such as SEQ ID NO: 1.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The percent identity between the two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm. In some embodiments, the percent identity between two amino acid sequences is determined using the Needleman and Wunsch ((1970) J. Mol. Biol. 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In some embodiments, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

It is understood that the molecules and compounds of the present embodiments may have conservative or non-essential amino acid substitutions, which do not have a substantial effect on their functions. The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Cells for use in the disclosed chemoprotective methods may be any suitable cell known to one of skill in the art. For example, the cells can be stem cells or immune cells. Non-limiting examples of stem cells include a cord blood cell, fetal stem cell, embryonic stem cell (ESC), hematopoietic stem cell (HSC), hematopoietic progenitors cell, pluripotent stem cell (PSC), induced PSC (iPSC), or a cell derived therefrom. In some embodiments, the immune cell is a T cell. In some embodiments, the cells are CD34+ and/or CD4+. In some embodiments, the cells are mesenchymal stem cells, stromal stem cells, cord blood derived hematopoietic stem/progenitor cells, cord tissue derived stem/progenitor cells, iPSCs, HESCs, fetal tissue derived stem cells, CD4+ cells, and the like. In some embodiments, the stem cells are CD34+.

The compositions and methods described herein can be utilized in bone marrow transplant situations such as those described in WO2020/018413.

For example, in some embodiments, provided herein are methods for performing a bone marrow transplant in a patient in need thereof. Also are provided for methods for replacing a subject's bone marrow cells with a population of cells expressing a heterologous nucleic acid molecule expression cassette or a plurality of heterologous expression cassettes or with a cell that has had its genome edited and differs from the subject's genome. In some embodiments, the heterologous protein expressed is GCLM or a variant thereof. In some embodiments, these methods comprise administering to the patient one or more chemotherapeutic-resistant modified cells and administration of at least one dose of a chemotherapeutic agent. In certain embodiments, the dose is a non-myeloablative dose of a chemotherapeutic agent. In certain embodiments, the dose is a myeloablative dose of a chemotherapeutic agent. In some embodiments, the amount of the cells is a therapeutically effective amount. In some embodiments, the chemotherapy that is administered is busulfan. In some embodiments, the chemotherapeutic is one or more of: actinomycin, all-trans retinoic acid, azacitidine, azathioprine, bleomycin, bortezomib, busulfan, capecitabine, carboplatin, carmustine (BCNU), cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, lomustine (CCNU), mechlorethamine, melphalan, mercaptopurine, methotrexate, mitoxantrone, nimustin (ACNU) oxaliplatin, paclitaxel, pemetrexed, temezolamide, teniposide, thiotepa, tioguanine, topotecan, treosulfan, valrubicin, vemurafenib, vinblastine, vincristine, vindesine, and vinorelbine.

As provided for herein, in some embodiments, chemotherapeutic-resistant modified cells for use in the disclosed methods may be any suitable cell known to one of skill in the art. For example, the cells can be stem cells or immune cells. Non-limiting examples of stem cells include a cord blood cell, fetal stem cell, embryonic stem cell (ESC), hematopoietic stem cell (HSC), hematopoietic progenitors cell, pluripotent stem cell (PSC), induced PSC (iPSC), or a cell derived therefrom. In some embodiments, the immune cell is a T cell. In some embodiments, the cells are CD34+ and/or CD4+. In some embodiments, the cells are mesenchymal stem cells, stromal stem cells, cord blood derived hematopoietic stem/progenitor cells, cord tissue derived stem/progenitor cells, iPSCs, HESCs, fetal tissue derived stem cells, CD4+ cells, and the like. In some embodiments, the stem cells are CD34+.

Chemotherapeutic-resistant modified cells for use in the present methods may be cells from a patient (i.e., autologous cells), cells from a donor (i.e., allogeneic cells), or any combination thereof that have been modified to confer chemotherapeutic resistance through the expression of a heterologous protein, such as GCLM or a variant thereof. In certain embodiments, the methods provided herein further comprise isolating and/or purifying cells from a patient or a donor. In certain of these embodiments, the methods further comprise modifying the cells to be chemotherapeutic resistant. For example, in certain embodiments methods are provided for performing a bone marrow transplant in a patient in need thereof comprising isolating and/or purifying one or more cells from a patient or subject, modifying the one or more cells to be chemotherapeutic resistant as described herein, administering to the patient an effective amount of the one or more chemotherapeutic-resistant modified cells, and administering at least one dose of a chemotherapeutic agent.

Cells can be isolated by any method known to one of skill in the art, for example, based on expression/lack of expression of certain markers, rates of proliferation, and differentiation potential. In some embodiments, the cells are isolated based on the presence of a particular marker or combination of markers including, for example, CD34, CD4, Sca-1 CD38, CD123, CD90, CD45, CD133, antigen presenting cell markers (CD8, CD8alpha, CD11b, CD11c, CD103, CD205, CD24, CD115, CD117, CD135, CD11c$^{low}$, CD45RA, CD123, ILT-7, MHC class II, MHC Class II$^{low}$, TLR7, and/or TRL9). In some embodiments, the cells are isolated based on the absence of a particular marker, for example, CD3, CD14, CD19, CD56, and/or CD66b. In other embodiments, negative selection is performed for markers of, for example, T cells, B cells, granulocytic, and/or myelomonocytic cells. In some embodiments, cells are isolated based on the presence of Thy-1 alone or in combination with any other marker. In some embodiments, HSCs are isolated based on Lin$^{Thy1+Sca-1+}$ expression profile. In some embodiments, mouse HSCs can be isolated by the expression profile CD34$^-$, ScaI$^-$, c-kit$^+$. In some embodiments human HSCs can be isolated based on CD34 expression.

In some embodiments, the methods provided herein comprise administering one or more doses of a chemotherapeutic agent to the patient. In some embodiments, the dose is a non-myeloablative dose of a chemotherapeutic agent. In some embodiments, the dose is myeloablative. The chemotherapeutic agent can be any suitable chemotherapeutic agent known to one of skill in the art. Non-limiting examples of chemotherapeutic agents include actinomycin, all-trans retinoic acid, azacitidine, azathioprine, bleomycin, bortezomib, busulfan, capecitabine, carboplatin, carmustine (BCNU), cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, lomustine (CCNU), mechlorethamine, melphalan, mercaptopurine, methotrexate, mitoxantrone, nimustin (ACNU) oxaliplatin, paclitaxel, pemetrexed, temezolamide, teniposide, thiotepa, tioguanine, topotecan, treosulfan, valrubicin, vemurafenib, vinblastine, vincristine, vindesine, and vinorelbine.

In some embodiments, the methods provided herein comprise administering to the subject an effective amount of the chemotherapeutic-resistance modified cells and a non-myeloablative dose of a chemotherapeutic agent. The modified cells and chemotherapeutic agent can be administered by any appropriate route, which will be apparent to the skilled person depending on the disease or condition to be treated. Typical routes of administration include intravenous, intra-arterial, intramuscular, subcutaneous, intracranial, intranasal, intradermal, oral or intraperitoneal.

In some embodiments, about $1\times10^8$ to about $1\times10^{11}$ cells per m$^2$ of body surface area of the subject are administered to the subject. The cells can be administered to an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) cells per injection, or any ranges between any two of the numbers, end points inclusive. In some embodiments, about $5\times10^6$/kg to about $10\times10^6$/kg of cells are used for a HSC transplant.

In other embodiments, the subject can be administered from about 1000 cells/injection/m$^2$ to up to about 10 billion cells/injection/m$^2$, such as at about, at least about, or at most about, $1\times10^8$/m$^2$, $1\times10^7$/m$^2$, $5\times10^7$/m$^2$, $1\times10^6$/m$^2$, $5\times10^6$/m$^2$, $1\times10^5$/m$^2$, $5\times10^5$/m$^2$, $1\times10^4$/m$^2$, $5\times10^4$/m$^2$, $1\times10^3$/m$^2$, $5\times10^3$/m$^2$ (and so forth) cells per injection, or any ranges between any two of the numbers, end points inclusive.

In other embodiments, the cells can be administered to such individual by relative numbers of cells, e.g., said individual can be administered about 1000 cells to up to about 10 billion cells per kilogram of the individual, such as at about, at least about, or at most about $1\times10^8$, $5\times10^7$, $1\times10^7$, $5\times10^6$, $1\times10^6$, $5\times10^5$, $1\times10^5$, $5\times10^4$, $1\times10^4$, $5\times10^3$, $1\times10^3$, (and so forth) cells per kilogram of the individual, or any ranges between any two of the numbers, end points inclusive.

In some embodiments, at least one non-myeloablative dose of a chemotherapeutic agent is administered to the patient. The administration of the chemotherapeutic agent can occur concurrently or sequentially with the administration of the modified cells. In some embodiments, at least one non-myeloablative dose of the chemotherapeutic agent is administered after administration of the modified cells. In some embodiments, a preconditioning step (also referred to herein as "pretreatment step") is performed prior to administration of the cells wherein the patient is administered at least one dose of a chemotherapeutic agent, for example, fludarabine or cyclophosphamide, prior to administration of the modified cells. In some embodiments, the preconditioning step is a non-myeloablative chemotherapeutic preconditioning step. In some embodiments, a preconditioning step is not performed prior to administration of the cells. It is contemplated that cells of the present disclosure will still be able to efficiently engraft into the patient's bone marrow even without the preconditioning step (e.g., fludarabine) prior to administration of the cells.

In some embodiments, the at least one non-myeloablative dose of a chemotherapeutic agent for a human subject or patient is a non-myeloablative dose of busulfan. In some embodiments, the non-myeloablative dose of cyclophosphamide is from about 0.1 mg/kg/day to about 8 mg/kg/day, about 0.1 mg/kg/day to about 7 mg/kg/day, about 0.1 mg/kg/day to about 6 mg/kg/day, about 0.1 mg/kg/day to about 5 mg/kg/day, about 0.1 mg/kg/day to about 4 mg/kg/day, about 0.1 mg/kg/day to about 3 mg/kg/day, about 0.1 mg/kg/day to about 2 mg/kg/day, about 0.1 mg/kg/day to about 1 mg/kg/day, about 0.5 mg/kg/day to about 8 mg/kg/day, about 0.5 mg/kg/day to about 7 mg/kg/day, about 0.5 mg/kg/day to about 6 mg/kg/day, about 0.5 mg/kg/day to about 5 mg/kg/day, about 0.5 mg/kg/day to about 4 mg/kg/day, about 0.5 mg/kg/day to about 3 mg/kg/day, about 0.5 mg/kg/day to about 2 mg/kg/day, about 0.5 mg/kg/day to about 1 mg/kg/day, about 1.0 mg/kg/day to about 8 mg/kg/day, about 1.0 mg/kg/day to about 7 mg/kg/day, about 1.0 mg/kg/day to about 6 mg/kg/day, about 1.0 mg/kg/day to about 5 mg/kg/day, about 1.0 mg/kg/day to about 4 mg/kg/day, about 1.0 mg/kg/day to about 3 mg/kg/day, about 1.0 mg/kg/day to about 2 mg/kg/day, about 2 mg/kg/day to about 8 mg/kg/day, about 2 mg/kg/day to about 7 mg/kg/day, about 2 mg/kg/day to about 6 mg/kg/day, about 2 mg/kg/day to about 5 mg/kg/day, about 2 mg/kg/day to about 4 mg/kg/day, about 2 mg/kg/day to about 3 mg/kg/day, about 3 mg/kg/day to about 8 mg/kg/day, about 3 mg/kg/day to about 7 mg/kg/day, about 3 mg/kg/day to about 6 mg/kg/day, about 3 mg/kg/day to about 5 mg/kg/day, about 3 mg/kg/day to about 4 mg/kg/day, about 4 mg/kg/day to about 8 mg/kg/day, about 4 mg/kg/day to about 7 mg/kg/day, about 4 mg/kg/day to about 5 mg/kg/day, about 6 mg/kg/day to about 4 mg/kg/day to about 5 mg/kg/day, about 5 mg/kg/day to about 8 mg/kg/day, about 5 mg/kg/day to about 7 mg/kg/day, about 5 mg/kg/day to about 6 mg/kg/day, about 6 mg/kg/day to about 8 mg/kg/day, about 6 mg/kg/day to about 7 mg/kg/day, or about 7 mg/kg/day to about 8 mg/kg/day. Although, the amounts and ranges are listed in a series, the amounts that can be administered can be done individually and also as the endpoints of the ranges. In some embodiments, the non-myeloablative dose is about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, or about 8 mg/kg. In some embodiments, the non-myeloablative dose is less than 8 mg/kg. The dose can be administered on a daily basis.

In some embodiments, a myeloablative dose is administered. In some embodiments, the myeloablative dose of busulfan is about 8 to about 12 mg/kg, which can be in a day.

In some embodiments, the non-myeloablative dose of the chemotherapeutic agent is administered every day for at least about 1 day, at least about 2 days, at least about 3 days, at least about 4 days, at least about 5 days, at least about 6 days, at least about 1 week, at least about 2 weeks, at least about 3 weeks, at least about 1 month, at least about 2 months, at least about 3 months, at least about 4 months, at least about 5 months, at least about 6 months, at least about 1 year, or longer.

In some embodiments, the non-myeloablative dose is provided for a period of time that does not result in cumulative toxicity. For example, the period of time that does not result in cumulative toxicity is a period of times less than about 1 year, less than about 6 months, less than about 3 months, less than about 2 months, less than about 1 month, less than about 3 weeks, less than about 2 weeks, less than about 1 week, less than about 6 days, less than about 5 days, less than about 4 days, less than about 3 days, or less than about 2 days.

In some embodiments, there is at least one break for a period of time between the administering of the cyclophosphamide-resistant modified cells and at least one non-myeloablative dose of a chemotherapeutic agent. For example, the period of time can be for about 2 days, about 3 days, about 4 days, about 5 days, about 6 days, about 1 week, about 2 weeks, about 3 weeks, about a month, about 2 months, about 3 months, about 6 months, about a year or more. In some embodiments, the period of time is about 3 days, about 7 days, about 10 days, and about 14 days.

In some embodiments, greater than about 60%, about 70%, about 80%, about 90%, about 95%, or 100% of the patient's bone marrow is replaced with the modified cells. In some embodiments, greater than about 60%, about 70%, about 80%, about 90%, about 95%, or 100% of the patient's bone marrow is replaced with the modified cells within about a year. In some embodiments, greater than about 60%, about 70%, about 80%, about 90%, about 95%, or 100% of the patient's bone marrow is replaced with the modified cells within about 6 months. In some embodiments, greater than about 60%, about 70%, about 80%, about 90%, about 95%, or 100% of the patient's bone marrow is replaced with the modified cells within about 5 months. In some embodiments, greater than about 60%, about 70%, about 80%, about 90%, about 95%, or 100% of the patient's bone marrow is replaced with the modified cells within about 4 months. In some embodiments, greater than about 60%, about 70%, about 80%, about 90%, about 95%, or 100% of the patient's bone marrow is replaced with the modified cells within about 3 months. In some embodiments, greater than about 60%, about 70%, about 80%, about 90%, about 95%, or 100% of the patient's bone marrow is replaced with the modified cells within about 2 months. In some embodiments, greater than about 60%, about 70%, about 80%, about 90%, about 95%, or 100% of the patient's bone marrow is replaced with the modified cells within about 1 month. In some embodiments, greater than about 60%, about 70%, about 80%, about 90%, about 95%, or 100% of the patient's bone marrow is replaced with the modified cells within about 2 weeks. In some embodiments, greater than about 60%, about 70%, about 80%, about 90%, about 95%, or 100% of the patient's bone marrow is replaced with the modified cells within about 1 week.

In some embodiments, the patient is not myeloablated and/or immunocompromised during the method. In some embodiments, the patient does not experience clinically relevant anemia, neutropenia, thrombocytopenia, pancytopenia, low platelets, low white blood cells, low red cells, or any combination thereof or related symptom(s).

In another embodiment, upon treatment with the cells and chemotherapeutic agent of the present disclosure, the subject or subject group may exhibit one or more of the following outcomes:

(i) an increase in white blood cells of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) as compared to a control;

(ii) an increase in granulocytes of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(iii) an increase in neutrophils of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;
(iv) an increase in lymphocytes of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;
(v) an increase in eosinophils of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;
(vi) an increase in monocytes of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;
(vii) an increase in basophils of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;
(viii) an increase in red blood cells of at least about 5%, at least about 10%, at least about 15%, at least about 20%, at least about 25%, at least about 30%, at least about 35%, at least about 40%, at least about 45%, at least about 50%, at least about 55%, at least about 60%, at least 65%, at least 70%, at least about 75%, at least 80%, at least 85%, at least about 90%, at least about 95%, or at least 99% (actual % change or median % change) compared to a control;
(ix) an increase in all three cellular components of the blood (red cells, white cells, and platelets) of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least about 90%, at least 95%, or at least 99% (actual % change or median % change) compared to a control;
(x) no relapse for a period of at least about 6 months, about 1 year, about 2 years, about 3 years, about 4 years, about 5 years, about 6 years, about 7 years, about 8 years, about 9 years, about 10 years, about 15 years, about 20 years, about 25 years, about 30 years, about 35 years, about 40 years, about 45 years, about 50 years, about 55 years, about 60 years, or longer;
(xi) an increase in relapse free survival of a patient of at least about 1 year, about 2 years, about 3 years, about 4 years, about 5 years, about 6 years, about 7 years, about 8 years, about 9 years, about 10 years, about 15 years, about 20 years, about 25 years, about 30 years, about 35 years, about 40 years, about 45 years, about 50 years, about 55 years, about 60 years, or longer as compared to a control; or
(xii) an increase in survival of a patient of at least about 1 year, about 2 years, about 3 years, about 4 years, about 5 years, about 6 years, about 7 years, about 8 years, about 9 years, about 10 years, about 15 years, about 20 years, about 25 years, about 30 years, about 35 years, about 40 years, about 45 years, about 50 years, about 55 years, about 60 years, or longer as compared to a control.

In certain embodiments of the methods provided herein, the chemotherapeutic-resistant modified cells may comprise one or more additional modifications unrelated to chemotherapeutic resistance. For example, in certain embodiments, the cells may be further modified to express additional HIV/disease-specific modifications. Accordingly, in certain embodiments the bone marrow transplant methods provided herein further comprise incorporating one or more additional modifications, including one or more HIV/disease-specific modifications. For example, in certain embodiments, methods are provided for performing a bone marrow transplant in a patient in need thereof comprising isolating and/or purifying one or more cells from a patient or subject, modifying the one or more cells to be chemotherapeutic resistant as described herein, incorporating one or more additional modifications into the one or more cells, administering to the patient an effective amount of the one or more chemotherapeutic-resistant modified cells, and administering at least one dose of a chemotherapeutic agent. In some embodiments, the dose is a non-myeloablative dose of a chemotherapeutic agent.

In some embodiments, the modified cells are further modified to be HIV resistant. For example, the modified cell can be further modified to express at least one mutant HIV co-receptor that confers resistant to HIV infection, a mutation or plurality of mutations of at least one HIV co-receptor, expression of at least one HIV fusion inhibitor, or any combination thereof. In some embodiments, the cells are modified to express a molecule that inhibits or reduces the expression of a HIV co-receptor. In some embodiments, the molecule is an antisense molecule. In some embodiments, the cells are modified to express shCCR5, shCXCR4, a GP-41 fusion inhibitor, C46 fusion inhibitor, a C34 fusion inhibitor, any other C-peptide fusion inhibitor, or any combination thereof. In some embodiments, the CCR5 mutation is the CCR5-delta 32 mutation. In some embodiments, both copies of the CCR5 gene in the cells are replaced with the CCR5-delta 32 mutation. In some embodiments, one copy of the CCR5 gene is replaced with the CCR5-delta 32 mutation.

The present disclosure provides cells that are modified to have chemotherapeutic resistance, for example cyclophosphamide resistance, and HIV resistance. In some embodiments, cells may be modified to have cyclophosphamide resistance and HIV resistance. The HIV-resistance may be conferred by reduced expression of at least one HIV co-receptor, a mutation or plurality of mutations of at least one HIV co-receptor, expression of at least one HIV fusion inhibitor, or any combination thereof. The HIV-resistance may be conferred from reduced expression of the CCR5 HIV co-receptor, reduced expression of the CXCR4 co-receptor, expression of a C-peptide fusion inhibitor (e.g., a C46 fusion inhibitor or a C34 fusion inhibitor) or any combination thereof.

The cells can also be modified to express any molecule of interest. The molecule of interest can be modified as determined by the user or the specific patient need.

In some embodiments the modified cells are administered with at least one other HIV therapy. Suitable other HIV therapies include any HIV therapy known to one of skill in the art. Non-limiting examples of other HIV therapies include and combination drugs (e.g., efavirenz/emtricitabine/tenofovir disoproxil fumarate (Atripla®), emtricitabine/rilpivirine/tenofovir disoproxil fumarate (Complera®), elvitegravir/cobicistat/emtricitabine/tenofovir disoproxil fumarate (Stribild®), and abacavir/dolutegravir/lamivudine (Triumeq®)), a nucleoside/nucleotide reverse transcriptase inhibitor (NRTI) (e.g., abacavir (Ziagen®), efavirenz/emtriacitabine/tenofovir disoproxil fumarate (Atripla®), lamivudine/zidovudine (Combivir®), emtriacitabine/rilpivirine/tenofovir disoproxil fumarate (Complera®), emtricitabine (Emtriva®), lamivudine (Epivir®), abacavir/lamivudine (Epzicom®), zidovudine (Retrovir®), abacavir/lamivudine/zidovudine (Trizivir), emtricitabine/tenofovire disoproxil fumarate (Truvada®), didanosine (Videx®), didanosine extended release (Videx EC®), tenofovir disoproxil fumarate (Viread®), and stavudine (Zerit®)), a non-nucleoside reverse transcriptase inhibitor (NNRTI), a protease inhibitor (e.g. tipranavir (Aptivus®), indinavir (Crixivan®), atazanavir/cobicistat (Evotaz®), saquinavir (Invirase®), lopinavir/ritonavir (Kaletra®), fosamprenavir (Lexiva®), ritonavir (Norvir®), darunavir/cobicistat (Prezcobix®), darunavir (Prezista®), atazanavir (Reyataz®), nelfinavir (Viracept®)), an entry inhibitor (e.g., enfuvirtide (Fuzeon®)), an integrase inhibitor (e.g., raltegravir (Isentress®), dolutegravir (Tivicay®), and elvitegravir (Vitekta®)), a chemokine co-receptor antagonists (CCR5 antagonists) (e.g., maraviroc (Selzentry®) or vicriviroc), a cytochrome P4503A inhibitor, and immune-based therapies (e.g., hydroxychloroquine sulfate (Plaquenil). In some embodiments, the modified cells and the at least one other HIV therapy are administered simultaneously. In other embodiments, the modified cells and the at least one other HIV therapy are administered sequentially. In some embodiments, administration of at least one of the above-mentioned other HIV therapies is expressly excluded, for example, in some embodiments a NRTI is expressly excluded. In some embodiments, no other HIV therapy is administered other than the modified cells disclosed herein and at least one non-myeloablative dose of a chemotherapeutic agent (e.g., busulfan).

The cells, chemotherapeutic agent, and optionally, other HIV therapies can be administered once to a patient with HIV or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In some embodiments, methods of treating a patient with HIV are provided. In some embodiments, the methods comprise mobilizing the patients CD34$^+$ stem cells out of the marrow and into the periphery. In some embodiments, the cells are mobilized by the administration of G-CSF (Granulocyte-colony stimulating factor). G-CSF can be administered as, for example, a 1, 2, 3, 4, or 5 day regimen. In some embodiments, the G-CSF is administered for 3-5 days. The mobilized cells can be captured using methodology, such as apheresis. In some embodiments, the isolation of the cells, by, for example, apheresis is performed once the CD34$^+$ cell count is or exceeds 10.0 to 20.0×10$^6$/kg body weight. In some embodiments, the cell count is or exceeds 5.0 to 25.0×10$^6$/kg body weight. Although Cd34+ cells are used as the marker to capture the cells for transduction, other cell markers can be used, such as those described herein. For example, the cells that are used are isolated based on the presence of a particular marker or combination of markers including, for example, CD34, CD4, Sca-1 CD38, CD123, CD90, CD45, CD133, antigen presenting cell markers (CD8, CD8alpha, CD11b, CD11c, CD103, CD205, CD24, CD115, CD117, CD135, CD11c$^{low}$, CD45RA, CD123, ILT-7, MHC class II, MHC Class II$^{low}$, TLR7, and/or TRL9). In some embodiments, the cells are isolated based on the absence of a particular marker, for example, CD3, CD14, CD19, CD56, and/or CD66b. In other embodiments, negative selection is performed for markers of, for example, T cells, B cells, granulocytic, and/or myelomonocytic cells. In some embodiments, cells are isolated based on the presence of Thy-1 alone or in combination with any other marker. In some embodiments, HSCs are isolated based on Lin$^-$Thy1$^+$ Sca-1$^+$ expression profile. In some embodiments, mouse HSCs can be isolated by the expression profile CD34$^-$, Sca1$^+$, c-kit$^+$. In some embodiments human HSCs can be isolated based on CD34 expression. In some embodiments, the isolated cells are CD34+ or CD4+, or any combination thereof.

In some embodiments, the methods comprise centrifuging the collection of cells. This can be done, for example, to develop a cell rich pellet. The cells can then be re-suspended in a cryopreservation solution and frozen. In some embodiments, the cryopreservation solution comprises a solution of heparinized Plasmalyte solution and 10% DMSO (Dimethylsulfoxide). In some embodiments, the cells are initially stored at −4° C., then the sample will be frozen down to the target temperature of −156° C. (when stored in the vapor phase) to −196° C. (when stored in the liquid phase).

In some embodiments, the methods comprising infusing the transduced cells into the subject. In some embodiments, the subject has HIV. In some embodiments, the subject does not have HIV but is at high risk to obtain HIV and, therefore, desires to become HIV resistant.

In some embodiments, after the infusion of the modified cells, a non-myeloablative dose of the chemotherapeutic, such as busulfan is administered. Non-limiting examples of non-myeloablative doses are provided for herein.

In some embodiments, method of treating HIV in a subject are provided, the method comprising administering to the subject a population of cells heterologously expressing ALDH1 and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof. In some embodiments, the methods comprise administering at least one non-myeloablative dose of a chemotherapeutic agent. In some embodiments, the cells are autologous to the subject. In some embodiments, the cells are allogenic to the subject. In some embodiments, cells express shCCR5, shCXCR4, and/or a C-peptide fusion inhibitor. Sequences for these proteins can be found, for example, in WO2020/018413, which is hereby incorporated by reference in its entirety.

In some embodiments, methods of treating a patient with cancer are provided. In some embodiments, the methods comprise mobilizing the patients CD34$^+$ stem cells out of the marrow and into the periphery. In some embodiments, the cells are mobilized by the administration of G-CSF Granulocyte-colony stimulating factor). G-CSF can be administered as, for example, a 1, 2, 3, 4, or 5 day regimen. In some embodiments, the G-CSF is administered for 3-5 days. The mobilized cells can be captured using methodology, such as apheresis. In some embodiments, the isolation of the cells, by, for example, apheresis is performed once the CD34+ cell count is or exceeds 10.0 to 20.0×10⁶/kg body weight. In some embodiments, the cell count is or exceeds 5.0 to 25.0×10⁶/kg body weight. Although Cd34+ cells are used as the marker to capture the cells for transduction, other cell markers can be used, such as those described herein. For example, the cells that are used are isolated based on the presence of a particular marker or combination of markers including, for example, CD34, CD4, Sca-1 CD38, CD123, CD90, CD45, CD133, antigen presenting cell markers (CD8, CD8alpha, CD11b, CD11c, CD103, CD205, CD24, CD115, CD117, CD135, CD11c$^{low}$, CD45RA, CD123, ILT-7, MHC class II, MHC Class II$^{low}$, TLR7, and/or TRL9). In some embodiments, the cells are isolated based on the absence of a particular marker, for example, CD3, CD14, CD19, CD56, and/or CD66b. In other embodiments, negative selection is performed for markers of, for example, T cells, B cells, granulocytic, and/or myelomonocytic cells. In some embodiments, cells are isolated based on the presence of Thy-1 alone or in combination with any other marker. In some embodiments, HSCs are isolated based on Lin⁻Thy1⁺ Sca-1⁺ expression profile. In some embodiments, mouse HSCs can be isolated by the expression profile CD34⁻, Sca1⁺, c-kit⁺. In some embodiments human HSCs can be isolated based on CD34 expression. In some embodiments, the isolated cells are CD34+ or CD4+, or any combination thereof.

In some embodiments, the methods comprise centrifuging the collection of cells. This can be done, for example, to develop a cell rich pellet. The cells can then be re-suspended in a cryopreservation solution and frozen. In some embodiments, the cryopreservation solution comprises a solution of heparinized Plasmalyte solution and 10% DMSO (Dimethylsulfoxide). In some embodiments, the cells are initially stored at −4° C., then the sample will be frozen down to the target temperature of −156° C. (when stored in the vapor phase) to −196° C. (when stored in the liquid phase).

In some embodiments, the methods comprise transducing the isolated cells to become resistant to a chemotherapeutic agents, such as busulfan. As described herein, chemotherapeutic resistance can be achieved by the expression of GCLM. The GCLM can be introduced to the selected cells through the use of a vector (as described throughout the present specification), such as the use of a lentival vector. The GCLM can be operably connected to a promoter that can be cell specific. In some embodiments, the promoter is CD34 promoter. In some embodiments, the promoter is a hCD34 promoter. In some embodiments, the promoter is a hCD4 promoter. In some embodiments, the sequence of GCLM is expressed as a protein as provided in SEQ ID NO: 1. In some embodiments, GCLM is encoded by a nucleic acid molecule comprising the sequence of SEQ ID NO: 2 or the coding region thereof. Due to the degenerate nature of the genetic code the sequence of SEQ ID NO: 2 is provided as a non-limiting example and other nucleic acid molecules can be used to encode for the expression of a protein comprising SEQ ID NO: 1. In some embodiments, the GCLM comprises 1-10 conservative substitutions that do not change the function of GCLM. In some embodiments, the expressed GCLM is substantially identical to SEQ ID NO: 1.

The expression of GCLM in the vector can also be driven by an enhancer element. For example, the enhancer element can be a CD3E enhancer.

In some embodiments, CD34⁺ cells can be isolated by magnetic bead separation. Lentiviral vector-mediated human CD34+ cell transduction can include, for example, a 24 h prestimulation of cells in media with the addition of the cytokines Stem Cell Factor (SCF), Fms-related tyrosine kinase 3 ligand (FLT3L), thrombopoietin (TPO), IL-6, IL-2, IL-3, fibronectin, or any combination thereof. In some embodiments, the cells are then contacted (infected) with the lentivirus expressing the GCLM. The contacting can be performed in the presence of the cytokines of SCF, FLT3L and TPO (each 100 ng ml⁻¹) in serum-free X-Vivo 10 media. The cells can then be optionally frozen or not frozen. In some embodiments, the cell are not contacted with an AAV or AV vector.

In some embodiments, the methods comprising infusing the transduced cells into the subject. In some embodiments, the subject has cancer. In some embodiments, after the infusion of the modified cells, a non-myeloablative dose of the chemotherapeutic, such as busulfan, is administered. In some embodiments, the dosage is a dose of 50-200 mg and is given daily. In some embodiments, the non-myeloablative dose of busulfan is from about 0.15 mg/kg/day to less than 2.5 mg/kg/day, from about 0.4 mg/kg/day to about 1.7 mg/kg/day, or from about 0.8 mg/kg/day to about 1.5 mg/kg/day. In some embodiments, the non-myeloablative dose of busulfan is about 0.15 mg/kg/day, about 0.2 mg/kg/day, about 0.25 mg/kg/day, about 0.3 mg/kg/day, about 0.35 mg/kg/day, about 0.4 mg/kg/day, about 0.45 mg/kg/day, about 0.5 mg/kg/day, about 0.55 mg/kg/day, about 0.6 mg/kg/day, about 0.65 mg/kg/day, about 0.7 mg/kg/day, about 0.75 mg/kg/day, about 0.8 mg/kg/day, about 0.85 mg/kg/day, about 0.9 mg/kg/day, about 0.95 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, or about 2.4 mg/kg/day. In some embodiments, the non-myeloablative dose of busulfan is about 1.3 mg/kg/day. In some embodiments, the non-myeloablative dose of busulfan is from about 0.8 mg/kg/day to about 1.6 mg/kg/day, about 0.8 mg/kg/day, about 0.98 mg/kg/day, about 1.3 mg/kg/day, about 1.5 mg/kg/day, or about 1.6 mg/kg/day. In some embodiments, the non-myeloablative dose of busulfan is about 0.5 to about 2 mg/kg/day. The dose can be administered as provided for herein.

In some embodiments, the subject is also treated Fludarabine prior to the infusion of the modified cells. In some embodiments, on day 2 after collection (or day −5 before transplant), the patients are treated with fludarabine (15 mg/m²) for 5 days (until day −1 before the transplant). In some embodiments in the place of fludarabine, on day −1 before the transplant patients can be treated with 4 mg/kg busulfan. In some embodiments, the patients are treated day −2 before the transplant with a single dose of 1000 mg/m2 busulfan. However, after the infusion of the cells, the subject is treated with a non-myeloablative dose of busulfan as provided for herein.

In some embodiments, the subject is treated with a myeloablative of busulfan.

In some embodiments, a single nucleic acid molecule, such as a single vector, is used to encode for or express each of the nucleic acid molecules or proteins provided herein. In some embodiments, a single lentivirus comprises the nucleic acid sequences provided for herein. In some embodiments, a lentivirus is provided that comprises a single expression construct that encodes for GCLM, or a variant thereof. The promoters and response elements that operably connect the nucleic acid molecules that encode for GCLM are non-limiting and other promoters and response elements can be used. One of skill in the art would understand that the different promoters illustrated can be swapped with one another.

In some embodiments, the nucleic acid molecule comprises a 5' LTR and a 3' LTR that flanks the nucleic acid molecule encoding for GCLM protein. In some embodiments, the vector encodes another molecule of interest to be expressed in the same cell as the GCLM protein Thus, in some embodiments, the nucleic acid molecule comprises a sequence encoding for GCLM and a sequence of interest, which can be for example, any other protein, antisense, miRNA, or other nucleic acid molecule that is desired to be expressed in the bone marrow or the cells types provided for herein.

Provided herein in certain embodiments are chemotherapeutic-resistant modified cells as described above with regard to the disclosed methods, and the use of these cells in the disclosed methods. Also provided are methods of generating these cells by incorporating one or more modifications that confer chemotherapeutic resistance into a suitable cell, and, optionally, incorporating one or more additional modifications unrelated to chemotherapeutic resistance, e.g., additional disease-specific modifications.

Also provided herein in certain embodiments are compositions, including compositions for use in the methods provided herein, comprising at least one chemotherapeutic-resistant modified cell as provided herein. In some embodiments, the composition further comprises a pharmaceutically acceptable excipient, diluent, carrier, or any combination thereof.

The composition may comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like. Compositions may be prepared using conventional techniques that may include sterile isotonic saline, water, 1,3-butanediol, ethanol, 1,2-propylene glycol, polyglycols mixed with water, Ringer's solution, etc. In one aspect, a coloring agent is added to facilitate in locating and properly placing the composition to the intended treatment site.

Compositions may include a preservative and/or a stabilizer. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds (QACs), chlorbutanol, 2-ethoxyethanol, and imidurea.

To control tonicity, the composition can comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride and calcium chloride.

Compositions may include one or more buffers. Typical buffers include: a phosphate buffer; a Tris buffer; a borate buffer; a succinate buffer; a histidine buffer; or a citrate buffer. Buffers will typically be included at a concentration in the 5-20 mM range. The pH of a composition will generally be between 5 and 8, and more typically between 6 and 8 e.g. between 6.5 and 7.5, or between 7.0 and 7.8.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In some embodiments, the cell is part of a population of cultured cells (i.e., in vitro). In another embodiment, the cell is part of a population of cells of a subject (i.e., in vivo). For example, the modified cell and/or non-myeloablative dose of a chemotherapeutic agent may be delivered to a cell in vivo or a population of cells in vivo that form a tissue or organ in a subject for the purpose of treating or preventing cancer or the disease of interest. Alternatively, the modified cells and/or a non-myeloablative dose or myeloablative dose of a chemotherapeutic agent may be delivered to a cultured cell or a population of cultured cells for the purpose of conducting experiments to study its effect on a particular type of cell.

The composition can be included in an implantable device. Suitable implantable devices contemplated by this invention include intravascular stents (e.g., self-expandable stents, balloon-expandable stents, and stent-grafts), scaffolds, grafts, and the like. Such implantable devices can be coated on at least one surface, or impregnated, with a composition capable of treating or preventing cancer or other disease.

The compositions can be administered to a subject by any suitable mode and route. Non-limiting examples include internal, pulmonary, rectal, nasal, vaginal, lingual, intravenous, intraarterial, intramuscular, intraperitoneal, intracutaneous and subcutaneous routes.

The non-myeloablative or myeloablative dose of the chemotherapeutic can be administered orally, parenterally, intravenously, or as otherwise provided herein.

As provided herein, in some embodiments, cells, such as, but not limited to, stem cell or an immune cells are provided that comprise heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function. In some embodiments, the cell comprises heterologous GCLM. In some embodiments, the cell further comprises at least one additional heterologously expressed molecule of interest. In some embodiments, the stem cell are fetal stem cells, cord blood derived stem cells, hematopoietic stem cells (HSCs), pluripotent stem cells (PSCs), induced PSCs (iPSCs), embryonic stem cells (ESCs) or cells derived therefrom, such as CD34+ cells, CD90+ cells, CD45+ cells, CD17+ cells, CD45RA− cells, or any combination thereof. In some embodiments, the immune cells are T cells.

In some embodiments, the molecule of interest is a chimeric antigen receptor. In some embodiments, the T cell comprising the heterologous GCLM or other protein in the GSH pathway as described above, further comprises a chimeric antigen receptor (CAR). The CAR can be any CAR. The cell comprising the heterologous CAR and the heterologous GCLM or related GSH pathway gene product can be used to select for the CAR cells once administered to the patient. In some embodiments, the heterologous GCLM protein comprises an amino acid sequence of SEQ ID NO: 1 or a variant thereof or a sequence that is at least 90% identical to SEQ ID NO: 1 or is substantially identical to the amino acid sequence of SEQ ID NO: 1. In some embodiments, the cell does not heterologously express any other proteins that confer chemotherapeutic resistance. In some embodiments, the cell does not heterologously express ALDH. In some embodiments, the cell heterologously expresses GCLM and endogenously expresses GCLM.

In some embodiments a cell is provided that comprises a heterologous nucleotide molecule that encodes for the expression of glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof; and/or ii) an endogenous HIV co-receptor mutation or deletion. In some embodiments, the cell comprises a heterologous nucleotide molecule that encodes for GCLM. In some embodiments, the cell comprises a heterologous nucleotide sequence that encodes for a molecule reduces expression of the CCR5; encodes for a reduces expression of the CXCR4; encodes for the expression of a C-peptide fusion inhibitor; or any combination thereof. In some embodiments, the cell expresses shCCR5, shCXCR4, and/or a C-peptide fusion inhibitor, such as C44.

In some embodiments, the cell is modified to express the heterologous nucleotide sequences provided for herein with a non-viral gene transfer system. In some embodiments, the non-viral gene transfer system is a transposon gene transfer system. In some embodiments, the transposon gene transfer system is a Sleeping Beauty gene transfer system or a PiggyBac transposon gene transfer system. In some embodiments, the cell is modified with a CRISPR system to heterologously express GCLM and the other molecules of interest provided for herein.

In some embodiments, nucleic acid molecules encoding for heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof are provided. In some embodiments, the heterologous nucleotide sequence encodes a molecule that reduces expression of the CCR5; reduces expression of the CXCR4; encodes for the expression of a C-peptide fusion inhibitor; or any combination thereof. In some embodiments, the nucleic acid molecule encodes for the expression shCCR5, shCXCR4, and/or a C-peptide fusion inhibitor.

In some embodiments, vectors are provided for as described herein that comprise the nucleic acid molecules provided for herein. In some embodiments, the vector is a vector that can be used to produce a lentivirus. In some embodiments, as described herein, the vector is a lentiviral vector.

Also provided for herein, in some embodiments are compositions comprising one or more cells as provided for herein. In some embodiments, the composition is a pharmaceutical composition. Non-limiting examples of pharmaceutical compositions are provided for herein.

As described herein is a pharmaceutical composition comprising the cells as described in the disclosure and a pharmaceutically acceptable buffer or excipient.

The cells provided for herein can be used in various methods where chemoprotection can be useful. This can be used, for example, to administer genetically modified chemo-resistant cells to a patient and then use the chemotherapy to kill the non-chemo-resistant cells while the chemo-resistant cells are protected and are allowed to continue to reproduce. This can be used as a way to select for modified cells that express a heterologous protein, such as glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function and a molecule of interest. Additionally, it can be done without a molecule of interest, other than glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function, when the cells are being used to replace disease cells of the same cell type with normal or non-diseased cells that heterologously express glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function. This can be done, for example, in performing a bone marrow transplant or where a cell expresses a defective or mutated version of a protein that causes a pathology. Examples of pathologies are provided for herein and include, but are not limited to lysosomal storage diseases.

Accordingly, in some embodiments, methods for providing or improving chemoprotection in a target cell are provided. In some embodiments, the methods comprise providing a target cell with a heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function. The cell can, for example, be administered to a patient in need of such a target cell. In some embodiments, the heterologous protein is GCLM.

In some embodiments, methods, for providing or improving chemoprotection in a patient in need thereof are provided. In some embodiments, the methods comprise administering to the patient a cell expressing a heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function. In some embodiments, the heterologous protein is GCLM. In some embodiments, cell further comprises a heterologous molecule of interest, such as a protein or chimeric antigen receptor. Non-limiting examples of such proteins of interest are provided for herein. However, these are non-limiting examples and any molecule of interest could be used in the cell and the methods provided for herein.

In some embodiments, the heterologous expression of glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function allows for post-transplant in vivo selection.

In some embodiments, methods of conferring a chemotherapeutic resistant cell to a patient are provided. In some embodiments, the method comprises administering a cell expressing heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function to the patient. In some embodiments, the cell heterologously expresses GCLM.

In some embodiments, method of treating a patient with cancer are provided. In some embodiments, the method comprises administering to the patient a pharmaceutical composition comprising a cell expressing heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function with a non-myeloablative or a myeloablative dose of a chemotherapeutic. In some embodiments, the cell expresses heterologous GCLM. The non-myeloablative or a myeloablative dose of a chemotherapeutic can be administered prior to, after, or simultaneously with the cell expressing heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function, such as GCLM.

In some embodiments, the methods further comprise isolating stem cells or immune cells from the subject. In some embodiments, the isolated stem cells or immune cells are modified to express heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function, such as GCLM. In some embodiments, the cells are modified to express heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function by contacting the isolated cells with an expression vector comprising a nucleic acid molecule encoding for glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function.

In some embodiments, the vector is a viral vector a non-viral vector. In some embodiments, the vector is a lentiviral vector, an adenoviral vector, a plasmid, a retrovirus, a transposon, an episomal expression vector, modified RNA, or any combination thereof.

As provided for herein, the cells can be stem cells or immune cells. In some embodiments, the stem cell are, but not limited to, fetal stem cells, cord blood derived stem cells, hematopoietic stem cells (HSCs), pluripotent stem cells (PSCs), induced PSCs (iPSCs), embryonic stem cells (ESCs) or cells derived therefrom, such as CD34+ cells, CD90+ cells, CD45+ cells, CD17+ cells, CD45RA− cells, or any combination thereof. In some embodiments, the immune cells are T cells. In some embodiments, the T-cells further comprise a chimeric antigen receptor.

The modified cells can be autologous to the patient, allogeneic to the patient, or a combination thereof.

In some embodiments, the patient is undergoing gene therapy, cell therapy or CAR–T therapy.

As provided for herein, the chemoprotection provided can be against busulfan and/or naphthalene. In some embodiments, the methods provided for herein comprise administering to the patient (subject) a myeloablative dose or a non-myeloablative dose of busulfan and/or naphthalene.

In some embodiments, methods of performing a bone marrow transplant in a patient are provided. In some embodiments, the methods comprise administering to the patient a population of busulfan-resistant modified cells and at least one non-myeloablative or myeloablative dose of busulfan. In some embodiments, the population of busulfan-resistant modified cells comprises a heterologous gene encoding glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function. In some embodiments, the heterologous gene encodes GCLM. In some embodiments, the population of busulfan-resistant modified cells express GCLM. In some embodiments, the busulfan resistance of busulfan-resistant modified cells is conferred by expression of GCLM. In some embodiments, greater than 50% of the patient's bone marrow is replaced with the busulfan-resistant modified cells or cells derived therefrom within 6 months. In some embodiments, the patient has HIV, cancer, A1AT deficiency, WAS, Hurler Syndrome, Hunter Syndrome, Pompe Disease, Fabry Disease, Mucopolysaccharidoses disorder, MPS 1 H/S (Hurler/Scheie syndrome), MPS I H (Hurler disease), MPS II- (Hunter syndrome), MPS III A, B, C, and D (Sanfillipo syndrome), MPS I S (Scheie syndrome), MPS IV A and B (Morquio syndrome), MPS IX (hyaluronidase deficiency), MPS VII (Sly syndrome), MPS VI (Maroteaux-Lamy syndrome), lysosomal storage diseases, and Childhood cerebral adrenoleukodystrophy (cALD). In some embodiments, the cancer is a hematological cancer or malignancy. In some embodiments, the hematological cancer is, but not limited to, leukemia, acute lymphoblastic leukemia, acute myeloid leukemia, chronic lymphocytic leukemia, chronic myelogenous leukemia, hairy cell leukemia, lymphoma, aids-related lymphoma, cutaneous t-cell lymphoma, hodgkin lymphoma, hodgkin lymphoma, mycosis fungoides, non-hodgkin lymphoma, primary central nervous system lymphoma, sézary syndrome, t-cell lymphoma, waldenstrom macroglobulinemia, chronic myeloproliferative neoplasms, langerhans cell histiocytosis, multiple myeloma, myelodysplastic syndromes, or myelodysplastic/myeloproliferative neoplasms.

The busulfan resistance provided for herein and throughout can be transient, such that the heterologous expression of a gene product, such as GCLM, is temporary.

In some embodiments, the methods comprise contacting unmodified cells with an expression vector encoding for the expression of glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function to produce the busulfan-resistant modified cells. In some embodiments, the cell will express GCLM. In some embodiments, the expression vector is a viral vector or a non-viral vector. In some embodiments, the viral vector is a lentiviral or adenoviral vector. In some embodiments, the expression vector is a retrovirus, a transposon, an episomal expression vector, modified RNA, a plasmid, or any combination thereof.

In some embodiments, the at least one non-myeloablative or myeloablative dose of the chemotherapeutic agent is administered after administration of the modified cells. In some embodiments, the at least one non-myeloablative dose or myeloablative of the chemotherapeutic agent is a non-myeloablative or myeloablative dose of busulfan. In some embodiments, the non-myeloablative chemotherapeutic agent is administered every day for at least 1 week, at least 2 weeks, at least 3 weeks, at least 1 month, at least 2 months, at least 3 months, at least 4 months, at least 5 months, or at least 6 months. In some embodiments, the method further comprises not administering the non-myeloablative dose of the chemotherapeutic agent for a period of time between the administering of the busulfan-resistant modified cells and at least one non-myeloablative dose of the chemotherapeutic agent. In some embodiments, the period of time is selected from the group consisting of about 3 days, about 7 days, about 10 days, and about 14 days.

In some embodiments, greater than about 60%, about 70%, about 80%, about 90%, about 95%, or 100% of the patient's bone marrow is replaced with the modified cells.

In some embodiments, the patient is not myeloablated and/or immunocompromised as a result of the administration of the at least one non-myeloablative dose of the chemotherapeutic agent. In some embodiments, the patient does not experience clinically relevant anemia, neutropenia, thrombocytopenia, pancytopenia, low platelet, low white blood cells, or any combination thereof or related symptoms.

In some embodiments, the modified cells are resistant to HIV infection. In some embodiments, the modified cells heterologously express a mutation of at least one HIV co-receptor resistant to HIV infection, a mutation or plurality of mutations of at least one HIV co-receptor, at least one HIV fusion inhibitor, a molecule that reduces the expression of a HIV co-receptor, or any combination thereof. These can also be referred to as the molecule of interest other than the glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function. In some embodiments, the modified cells heterologously express shCCR5, shCXCR4, a C-peptide fusion inhibitor or any combination thereof. In some embodiments, the modified cells do not express a HIV co-receptor. In some embodiments, the modified cells do not express CCR5, CXCR4, or express CCR5-Δ32 or a combination thereof.

In some embodiments, methods of treating HIV in a subject are provided. In some embodiments, the methods comprise administering to the subject a population of cells heterologously expressing glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof; and at least one non-myeloablative dose of a chemotherapeutic agent. In some embodiments, the cells heterologously express GCLM. In some embodiments, the cells heterologously express shCCR5, shCXCR4, and/or a C-peptide fusion inhibitor. In some embodiments, the chemotherapeutic agent is busulfan.

In some embodiments, methods of expressing a molecule of interest in a subject are provided. In some embodiments, the methods comprise administering to the subject a cell that heterologously expresses heterologous glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function and the molecule of interest; and administering a non-myeloablative dose of busuflan. In some embodiments, the cell heterologously expresses GCLM. In some embodiments, the cell is CD34+ and/or CD4+, or as otherwise as provided herein, such as the immune cells or stem cells as provided for herein. In some embodiments, the molecule of interest is one that reduces expression of the CCR5; reduces expression of the CXCR4; encodes for the expression of a C-peptide fusion inhibitor; or any combination thereof. In some embodiments, the molecule of interest that reduces expression of the CCR5 is shCCR5. In some embodiments, the molecule of interest is a wild-type protein that is defective in A1AT deficiency, WAS, Hurler Syndrome, Hunter Syndrome, Pompe Disease, Fabry Disease, Mucopolysaccharidoses disorder, MPS 1 H/S (Hurler/Scheie syndrome), MPS I H (Hurler disease), MPS II-(Hunter syndrome), MPS III A, B, C, and D (Sanfillipo syndrome), MPS I S (Scheie syndrome), MPS IV A and B (Morquio syndrome), MPS IX (hyaluronidase deficiency), MPS VII (Sly syndrome), MPS VI (Maroteaux-Lamy syndrome), lysosomal storage diseases, and Childhood cerebral adrenoleukodystrophy (cALD). In some embodiments, the molecule of interest is a chimeric antigen receptor.

In some embodiments, methods of treating cancer in a patient are provided. In some embodiments, the methods comprise administering busulfan to a patient, wherein the patient has been administered a cell that heterologously expresses glutamate-cysteine ligase (GCL) modifier subunit GCLM, GCLC (GCL catalytic subunit), GCL (as a dimer or a full enzyme), or any other polypeptide in the GSH synthesis pathway that provide the equivalent function. In some embodiments, the cell heterologously expresses GCLM. In some embodiments, the method comprises administering the cell to the patient prior to administering the busulfan. In some embodiments, the busulfan is administered in a non-myeloablative dose. In some embodiments, the busulfan is administered in a myeloablative dose. In some embodiments, the cancer is a hematological cancer. In some embodiments, the hematological cancer is leukemia, acute lymphoblastic leukemia, acute myeloid leukemia, chronic lymphocytic leukemia, chronic myelogenous leukemia, hairy cell leukemia, lymphoma, aids-related lymphoma, cutaneous t-cell lymphoma, hodgkin lymphoma, hodgkin lymphoma, mycosis fungoides, non-hodgkin lymphoma, primary central nervous system lymphoma, sézary syndrome, T-cell lymphoma, waldenstrom macroglobulinemia, chronic myeloproliferative neoplasms, langerhans cell histiocytosis, multiple myeloma, myelodysplastic syndromes, or myelodysplastic/myeloproliferative neoplasms. In some embodiments, the cancer is an osteosarcoma.

The following examples are illustrative, but not limiting, of the compounds, compositions and methods described herein. Other suitable modifications and adaptations known to those skilled in the art are within the scope of the following embodiments.

EXAMPLE 1

In certain embodiments, methods and compositions utilizing Glutamate-cysteine ligase (GCL), which is an enzyme functions at the first step of Glutathione (GSH) synthesis pathway, are utilized, which contributes to busulfan clearance. The chemoprotective effects of glutamate-cysteine ligase (GCL) enzyme were analyzed by overexpressing its modifier subunit GCLM. It is noted that any suitable form may be used, including GCLM (GCL modifier subunit), GCLC (GCL catalytic subunit), GCL (as a dimer or a full enzyme) and other enzymes in the GSH synthesis pathway that serve the same function (See, Franklin et al., *Mol. Aspects Med.* 2009; 30(1-2):86-98.)

Methods

Jurkat, CEM, and Tf-1a cell lines were transduced with a lentiviral vector that expresses GCLM and green fluorescent protein (GFP) genes. Chemoprotection experiments were performed by incubating untransduced or mixed populations of (20% transduced, 80% untransduced) cells with busulfan in concentrations ranging from 0 to 200 µg/ml for 1, 2 or 4 hours. Cells were then incubated in busulfan-free culture for 24, 48, 72 and 96 h. Area under the concentration-time curve (AUC) was estimated by using trapezoidal rule from different times and concentrations of incubation. Pre- and post-exposure GSH levels were measured with fluorometric assays. Cell survival and proliferation at different timepoints were measured by Nucleocounter NC-200 and flow cytometry using PI and 7-AAD staining protocols. The chemoselection of protected GFP+ cells were evaluated by flow cytometry. Baseline GSH levels and GCLM expression were also measured in primary human HSPCs harvested from 3 different donors with fluorometric and RT-PCR assays.

The Cells are incubated with busulfan (0, 1, 2, 4, 6, 8, 10, 20, 40, 60, 80, 100 and 200 µg/ml) in serum-free media (RPMI) for 1, 2 and 4 hours. The cells were then washed with ice-cold buffer (PBS+0.5% HSA+0.1% glucose). The washed cells were cultured in RPMI+20% FBS. 24, 48, 72, and 96 h time-point measurements were done.

Results

GSH level changes between untransduced and transduced Jurkat, CEM and Tf-1a cells were 2.1, 1.7, and 1.9-fold respectively. Untransduced CEM cells were found to be most sensitive to busulfan exposure. Cell death and proliferation in all cell cultures were in an AUC-dependent manner. The 1.7-fold GSH activity in CEM cells conferred at least 3.5-fold protection against busulfan. At 72 h of the culture following 10 ug/ml busulfan exposure for 1 h, the purity of transduced CEM cells increased from 20% to 88%, and the viable transduced cell count increased from $30 \times 10^3$/ml to $84 \times 10^3$/ml. At doses higher than 10 ug/ml or longer exposure than 1 h, the transduced cells were 100% of the cultures after 72 h. Fold expansion in viable transduced cells at 72 h was similar to untreated transduced and untransduced controls (2.8, 3.2 and 3.3). GSH levels in transduced cells remained stable throughout the experiment, whereas GSH in untransduced cells was depleted after busulfan exposure. GSH levels in primary human HSPCs were similar to untransduced Tf-1a cells. Moreover, RT-PCR analysis showed that GCLM is not highly expressed in these cells.

EXAMPLE 2

Lack of sufficient engraftment in gene-modified hematopoietic stem/progenitor cells (HSPCs) therapies has been the biggest challenge. Usage of chemo-resistance gene against cytotoxic agents to select for these cells in vivo has been proposed. Clearance of busulfan—commonly used cytotoxic chemotherapy agent for conditioning regimens in HSPC transplants—is achieved by Glutathione (GSH) conjugation. Increased levels of GSH in the cytoplasm mediates busulfan toxicity. The first step and rate-limiting enzyme of GSH synthesis pathway involves glutamate-cysteine ligase (GCL) (FIG. 1). The results provided herein demonstrate that increasing the GCL enzymatic activity through overexpressing its modifier subunit GCLM was able to confer protection against busulfan toxicity in vitro.

Figure 2A:
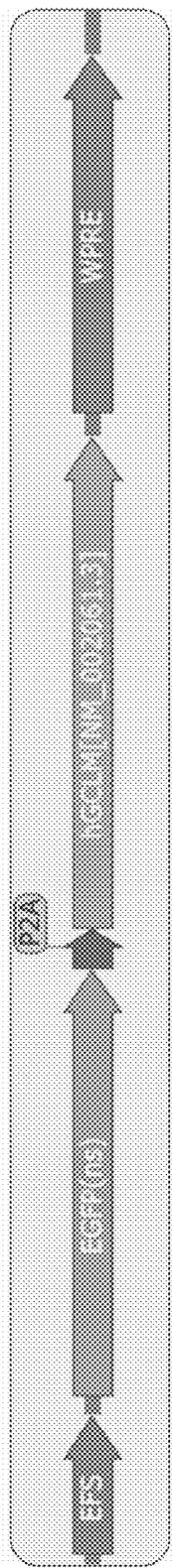
FIG. 2A illustrates a lentiviral engineered construct overexpressing human GCLM and GFP.
Figure 2B:
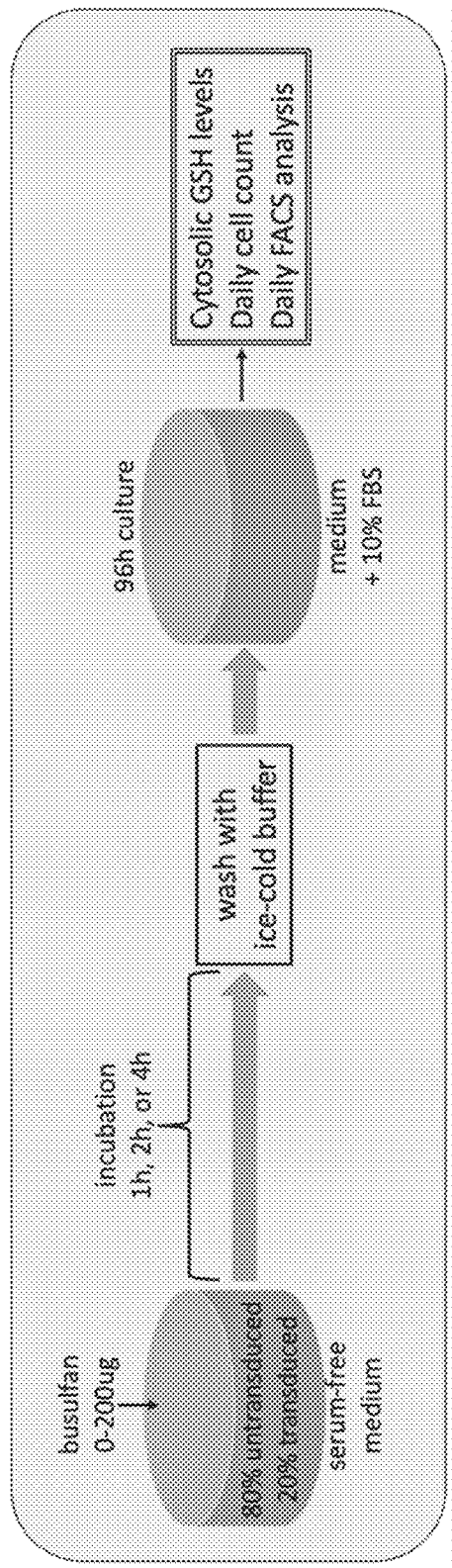
FIG. 2B illustrates embodiments provided for herein.

Jurkat, CEM, and TF-1a cell lines were transduced with a lentiviral vector that expresses GCLM and green fluorescent protein (GFP) genes (FIG. 2A). Chemoprotection experiments were performed by incubating untransduced or mixed populations of (20% transduced, 80% untransduced) cells with busulfan in concentrations ranging from low (2 to 10 ug/ml) to moderate and high (10 to 200 ug/ml) for 1 or 2 hours. Cells were then incubated and viable cell counts were documented in busulfan-free culture for the 24, 48, 72 and 96-hr timepoints (FIG. 2B). Pre- and post-transduction, and post-exposure GSH levels were measured with fluorometric assays by FACS analysis. Cell survival and proliferation were measured daily by Nucleocounter NC-200 and flow cytometry using PI and 7-AAD staining protocols. The chemo selection of protected GFP-positive cells were evaluated by flow cytometry.

Figures 3A, 3B:
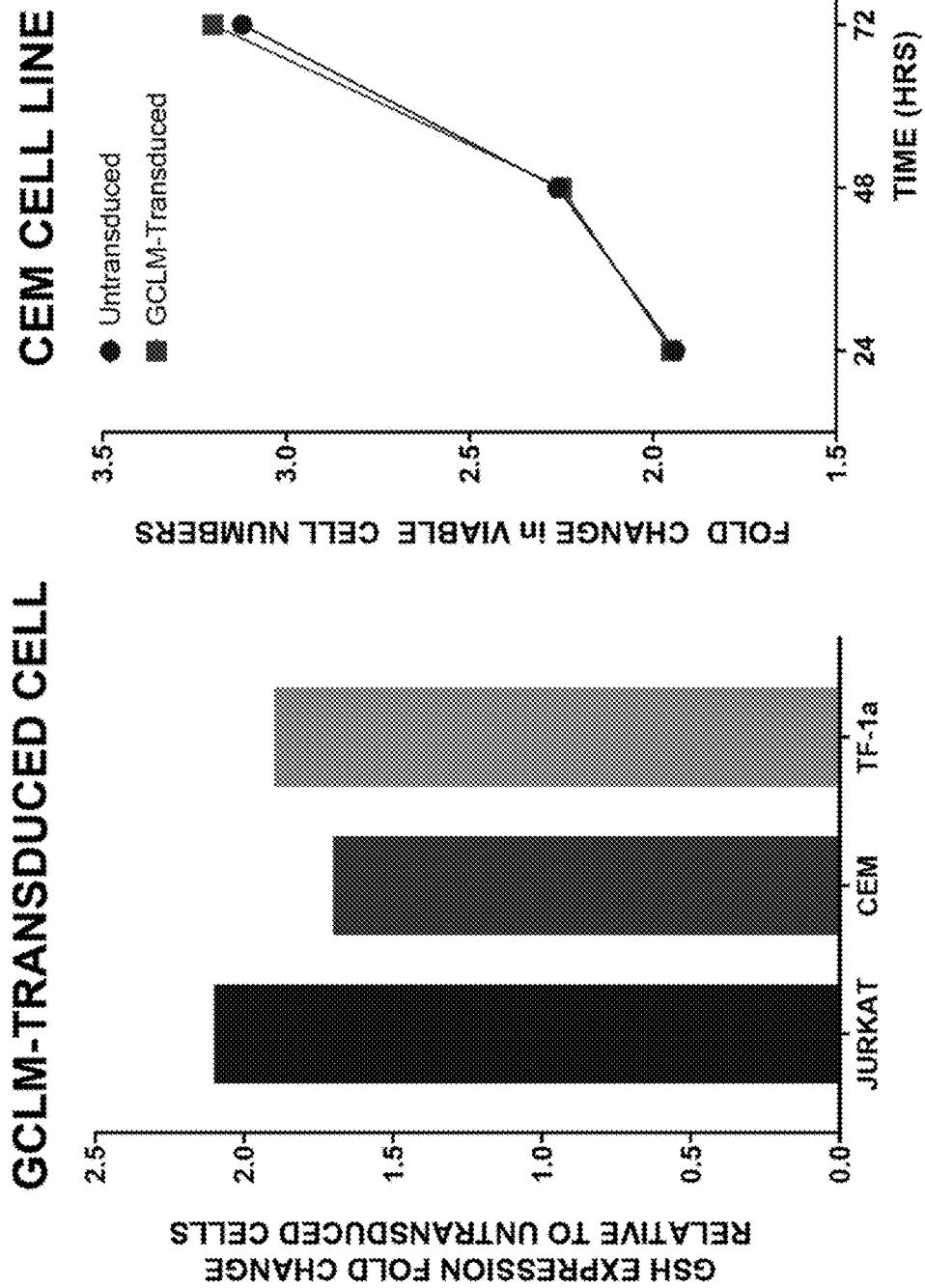
FIG. 3A and FIG. 3B illustrate unchanged proliferation rate and increased GSH in GCLM-transduced cells. GSH level changes between untransduced and transduced Jurkat, CEM and TF-1a cells were 2.1, 1.7, and 1.9-fold, respectively. Untransduced CEM cells were found to be most sensitive to busulfan exposure. There was no effect on cell viability and proliferation due to the overexpression of GCLM.
Figure 4:
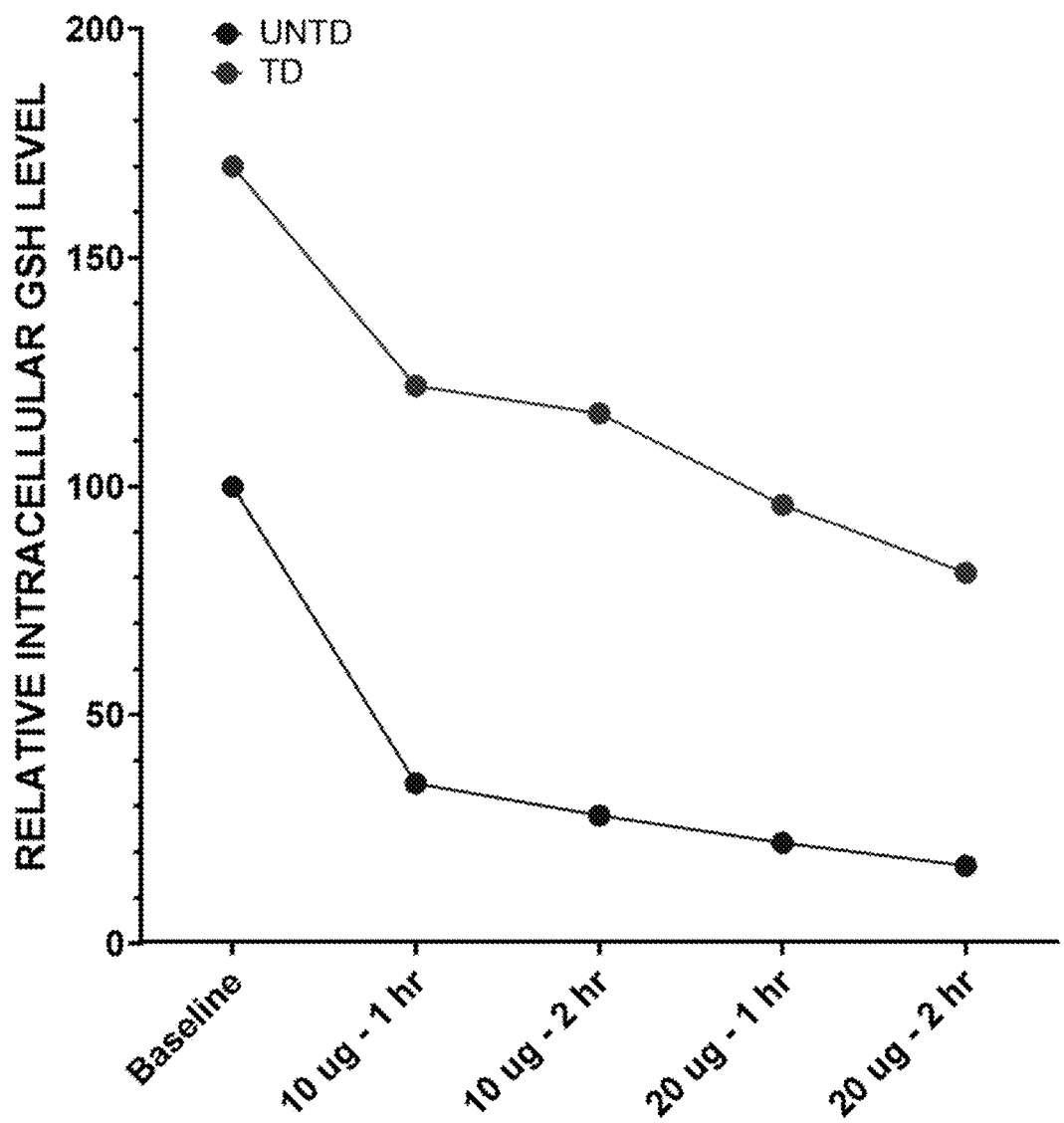
FIG. 4 illustrates GCLM-transduced CEM cells maintained high level of GSH.
Figure 5:
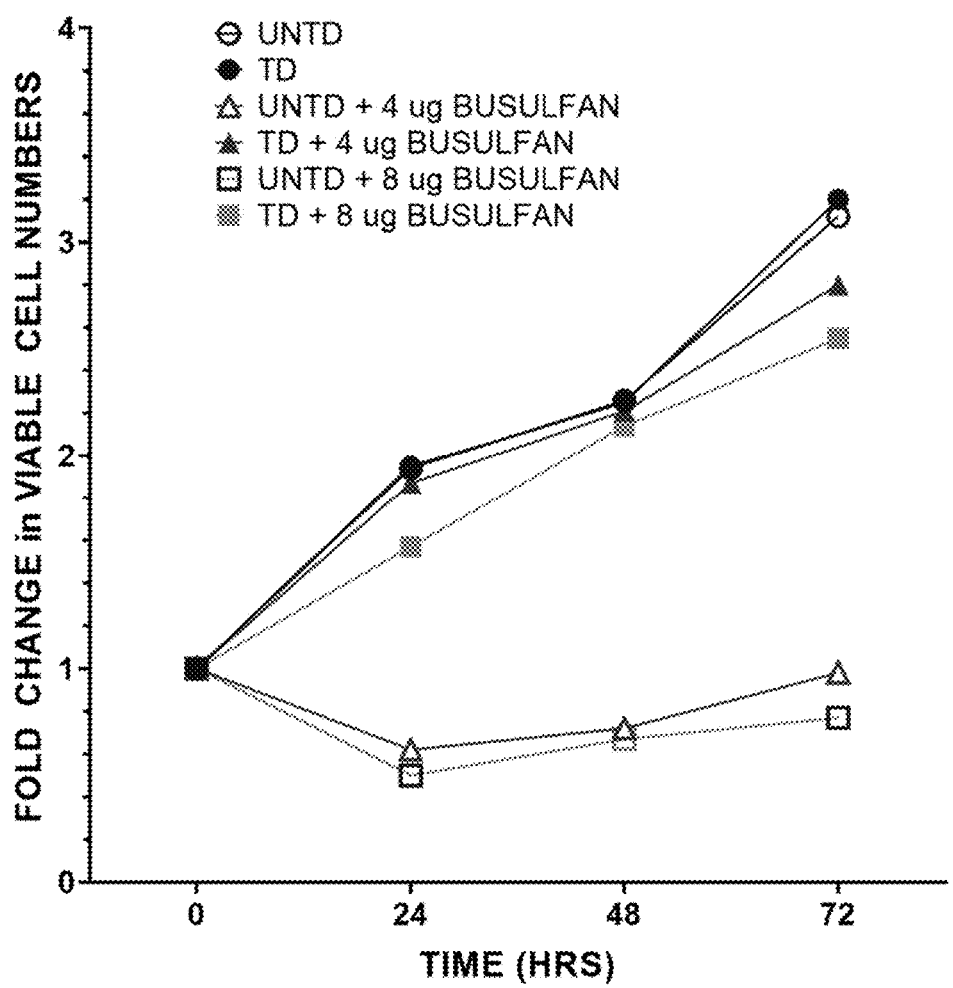
FIG. 5 illustrates GCLM-transduced cells being protected at low dosage of busulfan. GCLM transduced-CEM cells displayed at least 3.5 fold proliferate rates/protection against lower doses of busulfan exposure.
Figure 6:
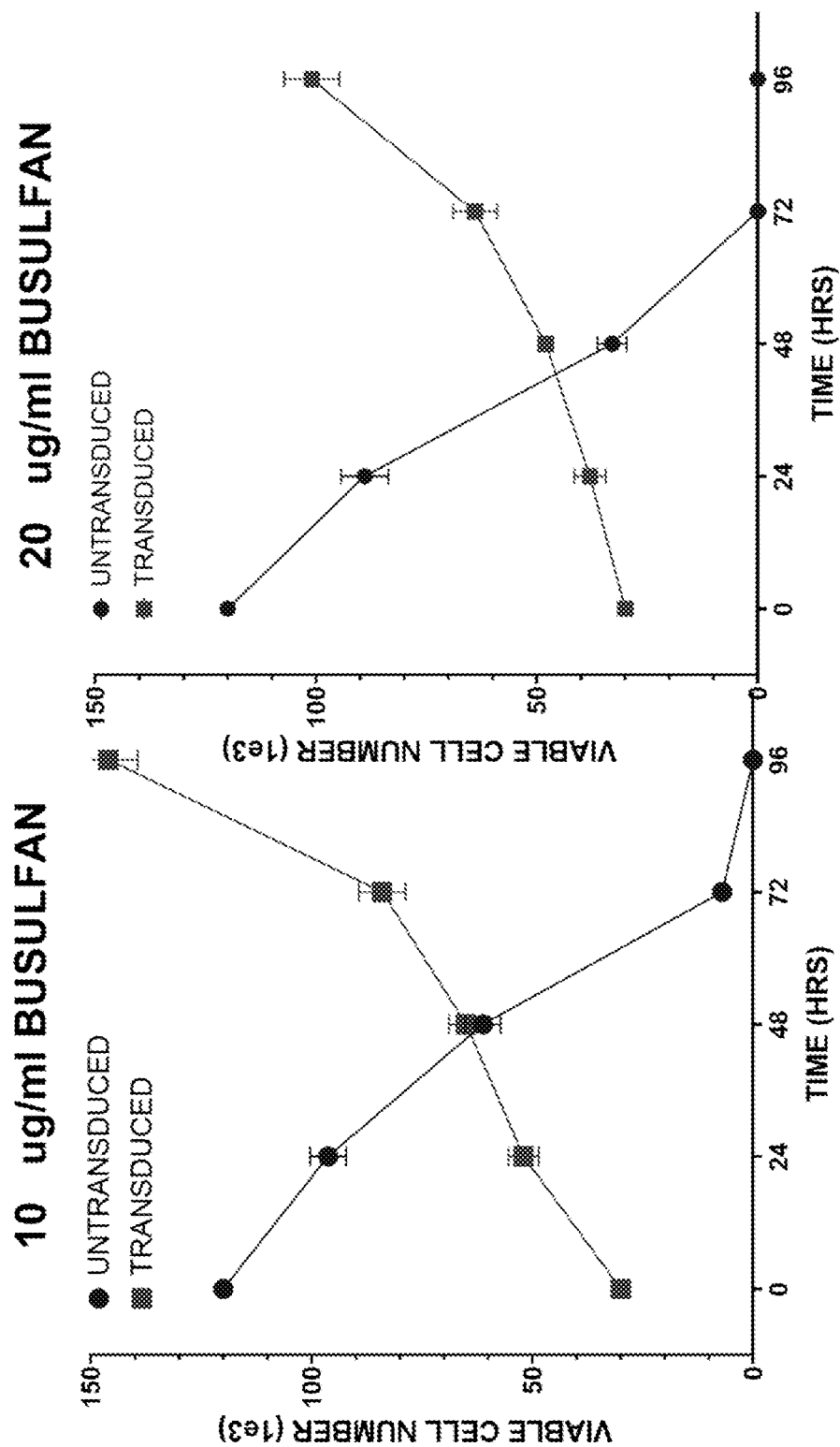
FIG. 6 illustrates GCLM-transduced cells being protected at higher dosage of busulfan. At higher doses of busulfan, the untransduced cells were all dead by 96 hours while the viable transduced cells had expanded 5- and 3-folds with 10 and 20 µg/ml of busulfan, respectively.
Figure 7:
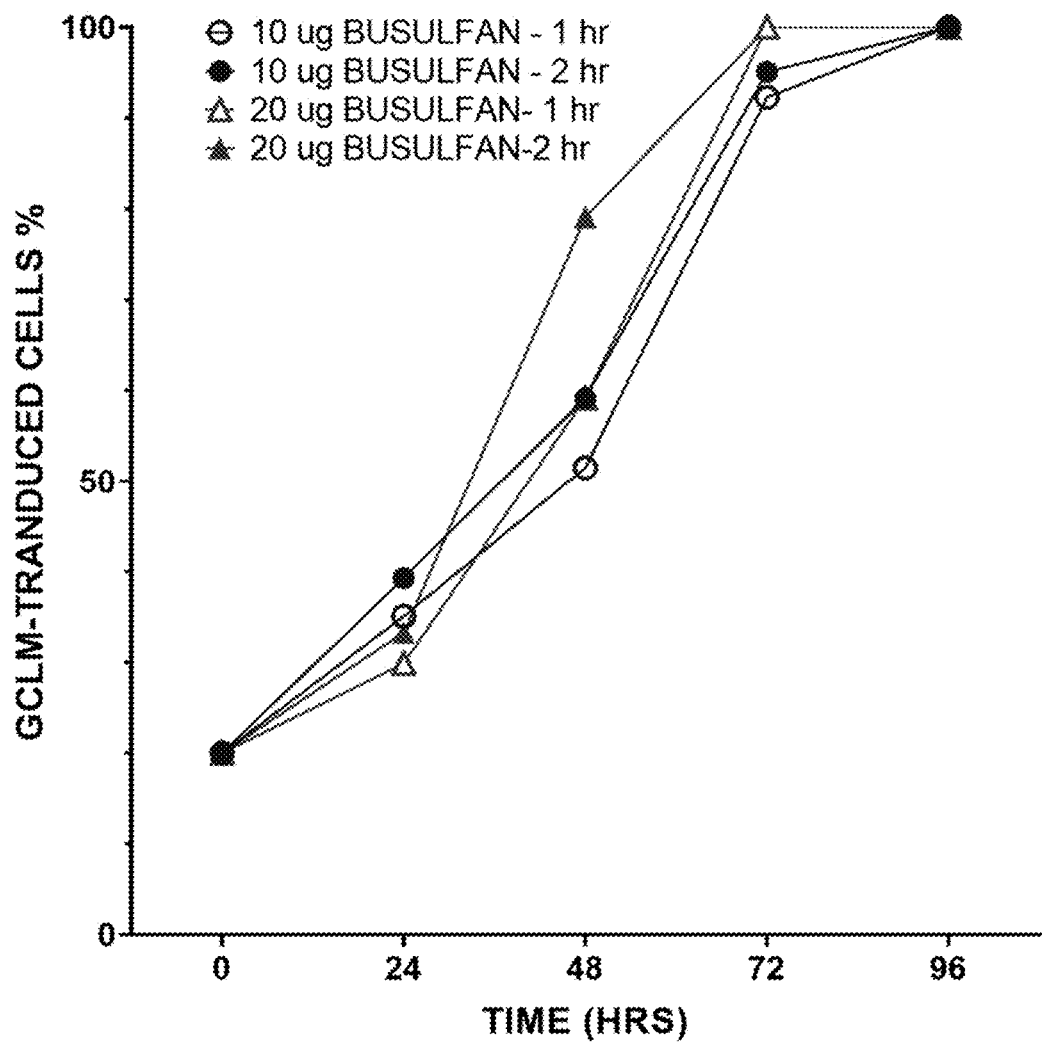
FIG. 7 illustrates proliferation of GCLM-transduced CEM cells after 1 or 2 hours exposure of busulfan. GCLM-transduced CEM cells were similarly protected from 10 or 20 µg/ml and 1-hr or 2-hr busulfan exposure and reached 100% from 20% initial transduced cell population b 96 hours.

The experiments demonstrated that GSH level increased in transduced Jurkat, CEM and TF-1a cells (FIG. 3A). There was no effect on cell viability and proliferation due to the overexpression of GCLM (FIG. 3B). GSH levels in transduced cells remained stable throughout the experiment, whereas GSH in untransduced cells was depleted after busulfan exposure (FIG. 4). Increased GSH activity in GLCM-transduced-CEM cells rendered at least 3.5-fold protection against busulfan at lower doses (FIG. 5). At higher doses (10 or 20 ug/ml) of busulfan exposure, it also exhibited protection and proliferation of the transduced cell populations (FIG. 6). Moderate levels of busulfan exposure achieved selection of chemo-protected cells and 100% transduced cell population in 72-96 h (FIG. 7)

These results demonstrate that increased expression GCL modifier subunit alone confers substantial chemoprotection against busulfan at multiple varying doses and times of exposure. This indicates that GCLM transgene expression can be used for busulfan protection, hence selection of genetically modified cells. As discussed herein, one of the biggest obstacles in gene-modified autologous HSPC transplants is lack of sufficient engraftment. Busulfan is an agent that has higher toxicity on bone marrow stem cells and limited toxicity to other organs. In gene-modified autologous non-myeloablative bone marrow transplants, GCLM gene also could be utilized to increase the engraftment rate of gene-modified stem cells using busulfan as an in vivo selection agent. These results were surprising and unexpected.

Conclusion

Accordingly, the emobdiments provided for herein show that increased expression of heterologous GCL modifier subunit alone can confer substantial chemoprotection against busulfan. This indicates that GCLM transgene expression can be used for post-transplant in vivo selection in gene modified autologous HSPC transplants.

Standard Methods

Standard methods in molecular biology are described Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, NY; Sambrook and Russell (2001) Molecular Cloning, 3rd ed., Cold Spring Harbor Laboratory Press, Cold Spring Harbor, NY; Wu (1993) Recombinant DNA, Vol. 217, Academic Press, San Diego, CA). Standard methods also appear in Ausbel, et al. (2001) Current Protocols in Molecular Biology, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, MO; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, NY; Harlow and Lane, supra). Standard techniques for characterizing ligand/receptor interactions are available (see, e.g., Coligan, et al. (2001) Current Protocols in Immunology, Vol. 4, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications of the embodiments in addition to those described herein will become apparent to those skilled in the art from the foregoing description and any accompanying figures. Such modifications are intended to fall within the scope of the appended claims.

What is claimed is:

1. A method for performing a bone marrow transplant in a patient having HIV, A1AT deficiency, WAS, Hurler Syndrome, Hunter Syndrome, Pompe Disease, Fabry Disease, Mucopolysaccharidoses disorder, MPS 1 H/S (Hurler/Scheie syndrome), MPS I H (Hurler disease), MPS II- (Hunter syndrome), MPS III A, B, C, and D (Sanfillipo syndrome), MPS I S (Scheie syndrome), MPS IV A and B (Morquio syndrome), MPS IX (hyaluronidase deficiency), MPS VII (Sly syndrome), MPS VI (Maroteaux-Lamy syndrome), lysosomal storage diseases, or Childhood cerebral adrenoleukodystrophy (cALD), the method comprising:
   administering to the patient a population of busulfan-resistant modified cells and at least one non-myeloablative dose of busulfan,
   wherein the population of busulfan-resistant modified cells comprises a heterologous gene encoding glutamate-cysteine ligase (GCL) modifier subunit GCLM, GCLC (GCL catalytic subunit), or GCL (as a dimer or a full enzyme).

2. The method of claim 1, wherein the population of busulfan-resistant modified cells express heterologous GCLM.

3. The method of claim 1, wherein the modified cells are resistant to HIV infection.

4. The method of claim 1, wherein the modified cells heterologously express a mutation of at least one HIV co-receptor resistant to HIV infection, a mutation or plurality of mutations of at least one HIV co-receptor, at least one HIV fusion inhibitor, a molecule that reduces the expression of a HIV co-receptor, or any combination thereof.

5. The method of claim 3, wherein the modified cells heterologously express shCCR5, shCXCR4, a C-peptide fusion inhibitor or any combination thereof.

6. A composition comprising a cell, the cell comprising a heterologous nucleotide molecule that encodes for the expression of glutamate-cysteine ligase (GCL) modifier subunit GCLM, GCLC (GCL catalytic subunit), or GCL (as a dimer or a full enzyme) and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof; and/or ii) an endogenous HIV co-receptor mutation or deletion.

7. A method of treating HIV in a subject, the method comprising administering to the subject a composition according to claim 6 and at least one non-myeloablative dose of a chemotherapeutic agent.

8. A method of expressing a molecule of interest in a subject having HIV, A1AT deficiency, WAS, Hurler Syndrome, Hunter Syndrome, Pompe Disease, Fabry Disease, Mucopolysaccharidoses disorder, MPS 1 H/S (Hurler/Scheie syndrome), MPS I H (Hurler disease), MPS II- (Hunter syndrome), MPS III A, B, C, and D (Sanfillipo syndrome), MPS I S (Scheie syndrome), MPS IV A and B (Morquio syndrome), MPS IX (hyaluronidase deficiency), MPS VII (Sly syndrome), MPS VI (Maroteaux-Lamy syndrome), lysosomal storage diseases, or Childhood cerebral adrenoleukodystrophy (cALD), the method comprising administering to the subject a cell that heterologously expresses heterologous glutamate-cysteine ligase (GCL) modifier subunit GCLM, GCLC (GCL catalytic subunit), or GCL (as a dimer or a full enzyme) and the molecule of interest; and administering a non-myeloablative dose of busulfan.

9. The method of claim 1, wherein the administering increases glutathione (GSH) levels in a target cell of the patient.

10. The method of claim 8, wherein the administering increases glutathione (GSH) levels in a target cell of the patient.

11. The method of claim 7, wherein the administering increases glutathione (GSH) levels in a target cell of the patient.

* * * * *